US011540701B2

(12) United States Patent
Arai et al.

(10) Patent No.: US 11,540,701 B2
(45) Date of Patent: Jan. 3, 2023

(54) MEDICAL HOLDING APPARATUS, MEDICAL ARM SYSTEM, AND DRAPE MOUNTING MECHANISM

(71) Applicant: Sony Corporation, Tokyo (JP)

(72) Inventors: Jun Arai, Tokyo (JP); Yohei Kuroda, Tokyo (JP); Masaru Usui, Tokyo (JP); Tetsuharu Fukushima, Tokyo (JP)

(73) Assignee: SONY CORPORATION, Tokyo (JP)

( * ) Notice: Subject to any disclaimer, the term of this patent is extended or adjusted under 35 U.S.C. 154(b) by 236 days.

(21) Appl. No.: 16/758,866

(22) PCT Filed: Oct. 25, 2018

(86) PCT No.: PCT/JP2018/039721
§ 371 (c)(1),
(2) Date: Apr. 24, 2020

(87) PCT Pub. No.: WO2019/087934
PCT Pub. Date: May 9, 2019

(65) Prior Publication Data
US 2021/0369092 A1 Dec. 2, 2021

(30) Foreign Application Priority Data

Nov. 1, 2017 (JP) .............................. JP2017-211782
Mar. 20, 2018 (JP) .............................. JP2018-052294

(51) Int. Cl.
*A61B 1/00* (2006.01)
*A61B 1/04* (2006.01)

(52) U.S. Cl.
CPC ........ *A61B 1/00149* (2013.01); *A61B 1/0016* (2013.01); *A61B 1/042* (2013.01)

(58) Field of Classification Search
CPC ... A61B 1/00149; A61B 1/0016; A61B 1/042; A61B 90/361
See application file for complete search history.

(56) References Cited

U.S. PATENT DOCUMENTS 5,836,869 A * 11/1998 Kudo ................. A61B 1/00006
600/173
6,464,631 B1 10/2002 Girke et al.
(Continued)

FOREIGN PATENT DOCUMENTS

JP 2017-093818 A 6/2017
JP 2017-93818 A 6/2017
(Continued)

OTHER PUBLICATIONS

International Search Report and Written Opinion dated Jan. 25, 2019 for PCT/JP2018/039721 filed on Oct. 25, 2018, 9 pages.

Primary Examiner — Aaron B Fairchild
(74) Attorney, Agent, or Firm — Xsensus LLP

(57) ABSTRACT

There is provided a medical holding apparatus including: a first actuator configured to cause a medical optical tool that guides light from a body cavity of a subject to a camera head during a surgical operation, to rotate about an optical axis of the medical optical tool and a rotation mechanism configured to support the camera head that acquires an image of the body cavity of the subject via the medical optical tool, the camera head being rotatable about the optical axis of the medical optical tool independently from the medical optical tool.

20 Claims, 21 Drawing Sheets

(56) References Cited

U.S. PATENT DOCUMENTS

| | | | | |
|---|---|---|---|---|
| 7,956,887 B2 * | 6/2011 | Hoeg | ................. | A61B 1/00126 |
| | | | | 348/208.99 |
| 2002/0161280 A1 * | 10/2002 | Chatenever | ............ | A61B 1/042 |
| | | | | 600/137 |

FOREIGN PATENT DOCUMENTS

| | | | | |
|---|---|---|---|---|
| JP | 2017093818 A | * | 6/2017 | |
| JP | 2017176611 A | * | 10/2017 | ............... A61B 1/00 |
| WO | 2014/155725 A1 | | 10/2014 | |
| WO | 2017/169118 A1 | | 10/2017 | |

* cited by examiner

MEDICAL HOLDING APPARATUS, MEDICAL ARM SYSTEM, AND DRAPE MOUNTING MECHANISM

CROSS REFERENCE TO RELATED APPLICATIONS

This application is based on PCT filing PCT/JP2018/039721, filed Oct. 25, 2018, which claims the benefit of Japanese Priority Patent Application JP 2017-211782, filed Nov. 1, 2017, and Japanese Priority Patent Application JP 2018-052294, filed Mar. 20, 2018, the entire contents of each of which are incorporated herein by reference.

TECHNICAL FIELD

The present disclosure relates to a medical holding apparatus, a medical arm system, and a drape mounting mechanism.

BACKGROUND ART

In the related art, for example, PTL 1 relates to an endoscopic operation system and endoscopic operation program and describes a configuration in which an image pickup unit and a vane motor are rotatable about a rotation shaft (paragraph 0037).

CITATION LIST

Patent Literature

PTL 1: WO 2014/155725

SUMMARY

Technical Problem

However, the technology described in PTL 1 only has a single rotational degree of freedom at a distal end of an endoscope and does not correspond to a perspective rotational operation in which an oblique viewing endoscope is caused to rotate about an axis in a state in which the top and bottom of a camera are held.

Accordingly, there has been a demand for enabling independent rotation of a medical optical apparatus such as a camera head and an oblique viewing endoscope about an optical axis.

Solution to Problem

According to an embodiment of the present disclosure, there is provided a medical holding apparatus including: a first actuator configured to cause a medical optical tool that guides light from a body cavity of a subject to a camera head during a surgical operation, to rotate about an optical axis of the medical optical tool; and a rotation mechanism configured to support the camera head that acquires an image of the body cavity of the subject via the medical optical tool, the camera head being rotatable about the optical axis of the medical optical tool independently from the medical optical tool.

In addition, according to an embodiment of the present disclosure, there is provided a medical arm system including:

a medical holding apparatus including a first actuator configured to cause a medical optical tool that guides light from a body cavity of a subject during a surgical operation to rotate about an optical axis of the medical optical tool, and a second actuator configured to cause a camera head that further acquires the image of the body cavity of the subject via the medical optical tool, the camera head being rotatable about the optical axis of the medical optical tool independently from the medical optical tool; and a supporting arm having a distal end to which the medical holding apparatus is fixed.

In addition, according to an embodiment of the present disclosure, there is provided a drape mounting mechanism including a drape mount connected to a medical optical tool for that guides light from a body cavity of a subject during a surgical operation and configured to rotate together with the medical optical tool about an optical axis of the medical optical tool.

Advantageous Effects of Invention

According to an embodiment of the present disclosure, as described above, independent rotation of a medical optical apparatus such as a camera head and an oblique viewing endoscope can be enabled.

Note that the effects described above are not necessarily limitative. With or in the place of the above effects, there may be achieved any one of the effects described in this specification or other effects that may be grasped from this specification.

DESCRIPTION OF EMBODIMENTS

Figure 1:
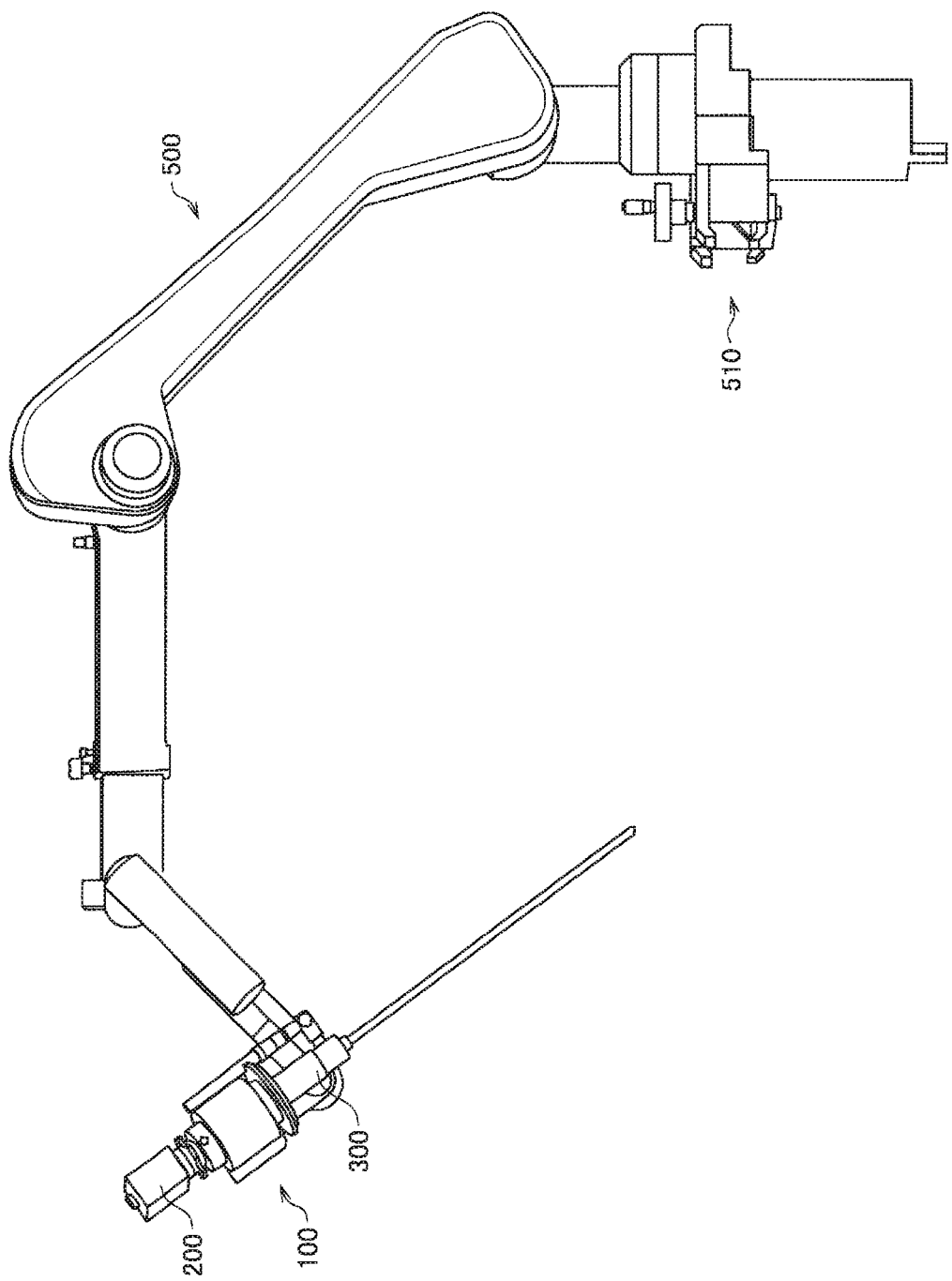
FIG. 1 is a schematic diagram illustrating a medical supporting arm apparatus 500 on which a medical holding apparatus according to an embodiment of the present disclosure is mounted.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be given in the following order.

1. Outline
2. Overall configuration example of medical holding apparatus
3. Specific configuration example of medical holding apparatus
4. Configuration example of connecting location of camera head
5. Configuration example of drape mounting mechanism
6. Connecting structure to arm side
7. Fixing structure of endoscope
8. Example of specific control using medical holding apparatus
   8.1 All-free operation mode
   8.2 Scope fixing-camera head rotating operation mode
   8.3 Camera head fixing-scope rotating operation mode
9. Application examples
10. Specific configuration example of medical supporting arm apparatus
11. Configuration example in which only actuator at endoscope side is provided

1. Outline

A general endoscope (rigid endoscope) mounted on a supporting arm apparatus has a single degree of freedom at a distal end and is unable to rotate while a camera head and the endoscope are separated. In the case of a forward viewing endoscope, it is not necessary to rotate each of the camera head and the endoscope while the camera head and the endoscope are separated. However, in the case of an oblique viewing endoscope, when the oblique viewing endoscope is caused to rotate about an axis, it is possible to obtain a wrap-around field of view or top, bottom, left, and right peripheral fields of view. On the other hand, in the case in which the oblique viewing endoscope is rotated about an axis, when a camera head rotates together with the oblique viewing endoscope, the direction of gravity tilts on a screen, and it becomes difficult to accurately perform a hand operation in coordination with vision (hereinafter also referred to as "hand-eye coordination"). In the present embodiment, a medical holding apparatus for connecting an endoscope and a camera head is provided so that the endoscope and the camera head can rotate relative to each other. In this way, especially when an oblique viewing endoscope is used, a field of view can be can be widened while hand-eye coordination is maintained.

2. Overall Configuration Example of Medical Holding Apparatus

FIG. 1 is a schematic diagram illustrating a medical supporting arm apparatus 500 on which a medical holding apparatus (holding unit) 100 according to an embodiment of the present disclosure is mounted. The medical supporting arm apparatus 500 has a clamp unit 510 for attachment to a surgical bed and is attached to the surgical bed through the clamp unit 510. The medical holding apparatus 100 is mounted at a distal end of the medical supporting arm apparatus 500 and holds an endoscope 300 such as a rigid endoscope (for example, an oblique viewing endoscope) at the distal end of the medical supporting arm apparatus 500. The medical holding apparatus 100 also holds a camera head 200 at an opposite side of the endoscope 300. That is, the medical holding apparatus 100 has a function of mounting the endoscope 300 and the camera head 200 and connecting the two. The camera head 200 picks up a subject image caught by the endoscope 300. The medical holding apparatus 100 may also hold medical optical apparatuses other than the endoscope 300, such as an exoscope and a medical microscope. A configuration of the medical supporting arm apparatus 500 will be described below.

3. Specific Configuration Example of Medical Holding Apparatus

Figure 2:
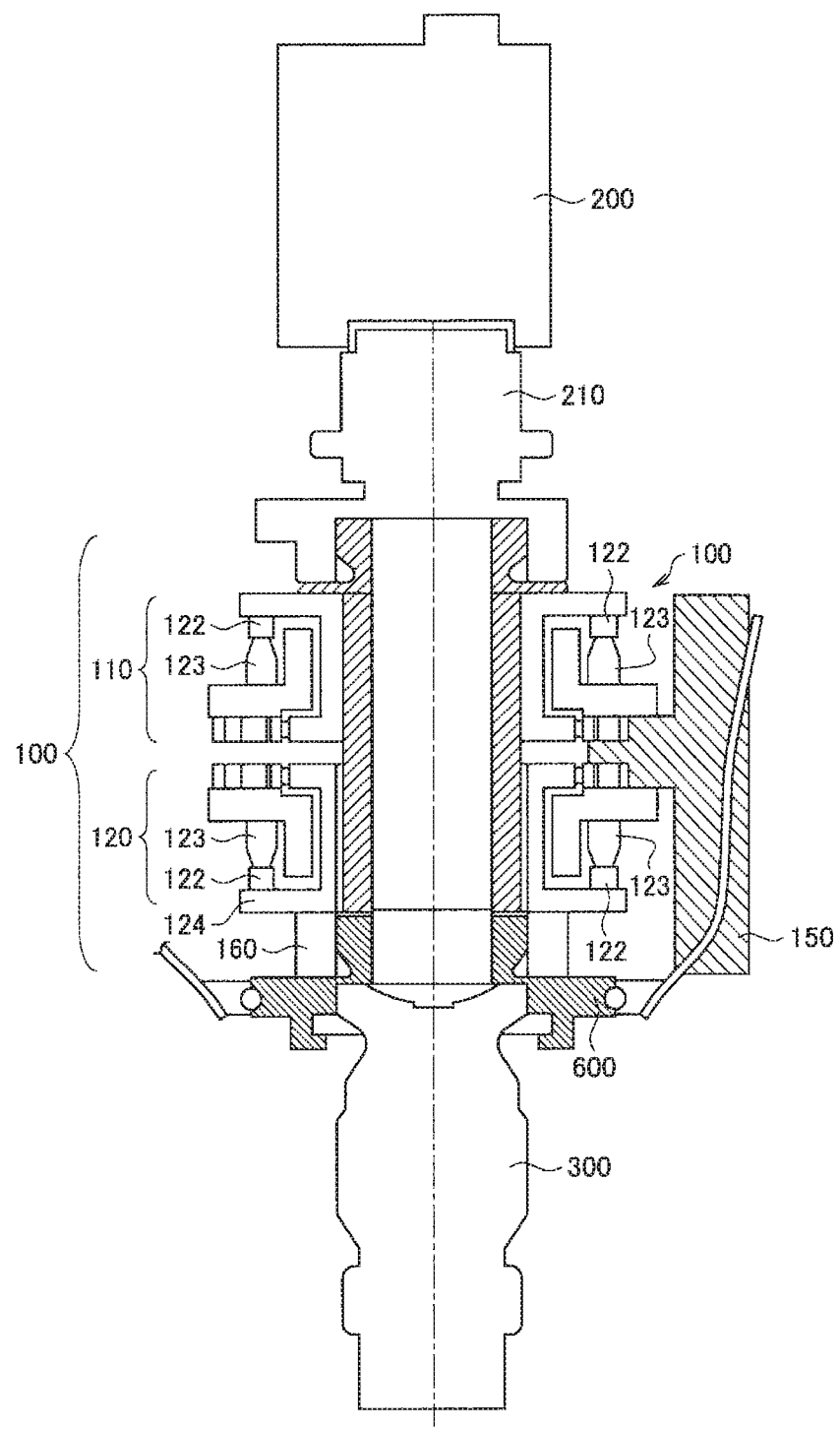
FIG. 2 is a cross-sectional diagram illustrating a configuration of the medical holding apparatus.

Next, a configuration of the medical holding apparatus 100 according to the present embodiment will be described with reference to FIG. 2. FIG. 2 is a cross-sectional diagram illustrating a configuration of the medical holding apparatus 100. The medical holding apparatus 100 includes two actuators 110 and 120, a lens barrel 140, and a lens (not illustrated) mounted at the lens barrel 140, and functions as an adaptor which secures two degrees of freedom of the camera head 200 and the endoscope 300 and connects the camera head 200 and the endoscope 300. Both of the two actuators 110 and 120 have a hollow, flat shape, and consequently, space saving as a whole can be realized.

Figure 3:
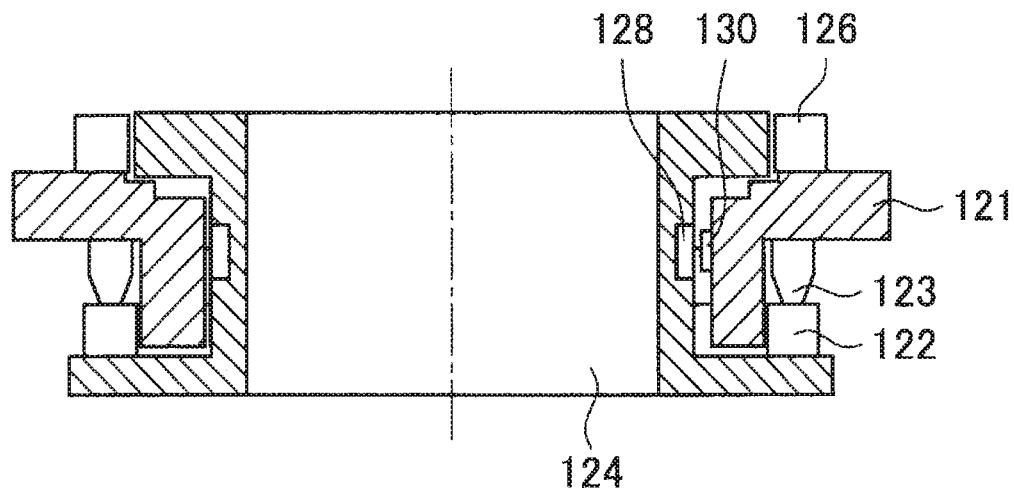
FIG. 3 is a cross-sectional diagram for describing a configuration of two actuators.

FIG. 3 is a cross-sectional diagram for describing a configuration of the two actuators 110 and 120. The two actuators 110 and 120 are formed as a unit, and are mounted with a ring type ultrasonic motor and a magnetic type encoder (magnet and IC). The type of the actuator is not particularly limited, and the actuator may also include a motor other than the ultrasonic motor. However, the actuator is preferably hollow and flat. Also, in order to connect the camera head 200 and the endoscope 300, the actuator preferably has an optical system, a camera, or the like disposed therein. For example, an actuator may also be formed by combining a motor and a speed reducer.

Since configurations of the two actuators 110 and 120 are basically the same, the configuration of the actuator 120 will be described herein. As illustrated in FIG. 3, the actuator 120 includes a stator 123, a rotor 122, an output unit 124, a bearing unit 126, and a ring-shaped magnet 128 and a sensor 130, which constitute a magnetic type encoder. Due to ultrasonic vibration of the stator 123, the rotor 122 rotates relative to the stator 123, and the output unit 124, which is fixed to the rotor 122, rotates.

The stator 123 is fixed to a fixing frame 121. The bearing unit 126 is fixed to the fixing frame 121. The output unit 124 is rotatably supported by the bearing unit 126.

The ring-shaped magnet 128 is mounted at an outer periphery of the output unit 124 and rotates together with the output unit 124. In accordance with the rotation of the magnet 128, a signal corresponding to a position of the magnet 128 is detected by the sensor 130, and consequently, a rotational position of the output unit 124 is detected. The configuration for detecting the rotational position of the output unit 124 is not limited thereto.

The output unit 124 has a cylindrical hollow shape, and the lens barrel 140 is inserted into the output unit 124. The lens barrel 140 is fixed to the output unit 124 of the actuator 110 and rotates together with the output unit 124 of the actuator 110. The lens disposed in the lens barrel 140 has a function of extending an optical system between the camera head 200 and the endoscope 300 and a function of connecting the optical system to the camera head 200. The lens may also be configured to be replaceable in accordance with the camera head 200 or the endoscope 300.

As illustrated in FIG. 1, in both of the two actuators 110 and 120, the fixing frame 121 is fixed to a frame 150 of the medical holding apparatus 100. The frame 150 is mounted at the distal end of the medical supporting arm apparatus 500. The actuator 110 is provided at the camera head 200 side, and the camera head 200 is mounted at a distal end of the lens barrel 140, which rotates relative to the stator 123, through an endoscope adaptor 210.

On the other hand, the actuator 120 is provided at the endoscope 300 side, and a predetermined space is provided between the output unit 124 of the actuator 120, which rotates relative to the stator 123, and the lens barrel 140. Therefore, the lens barrel 140 can freely rotate relative to the output unit 124 of the actuator 120.

An adaptor 160 is fixed to the output unit 124 of the actuator 120, and a drape mounting mechanism with a rotation mechanism is mounted at the adaptor 160. An end of the endoscope 300 at the camera head 200 side is mounted at the drape mounting mechanism. A drape configured to separate a clean area and an unclean area is mounted at a drape mounting unit 600 of the drape mounting mechanism.

In a case in which the drape mounting mechanism is not in use, the endoscope 300 may be directly mounted at the output unit 124 of the actuator 120 through the adaptor 160. The output unit 124 of the actuator 120 and the adaptor 160 may also be integrally formed.

According to the medical holding apparatus 100 configured as described above, by driving the actuator 110 provided at the camera head 200 side, the lens barrel 140 fixed to the output unit 124 rotates, and the endoscope adaptor 210 and the camera head 200 rotate together with the lens barrel 140. Therefore, the camera head 200 can be rotated relative to the frame 150.

Also, by driving the actuator 120 provided at the endoscope 300 side, the adaptor 160 and the drape mounting unit 600 rotate together with the output unit 124, and the endoscope 300 mounted at the drape mounting unit 600 integrally rotates with the drape mounting unit 600. Therefore, the endoscope 300 can be rotated relative to the frame 150.

Figure 4:
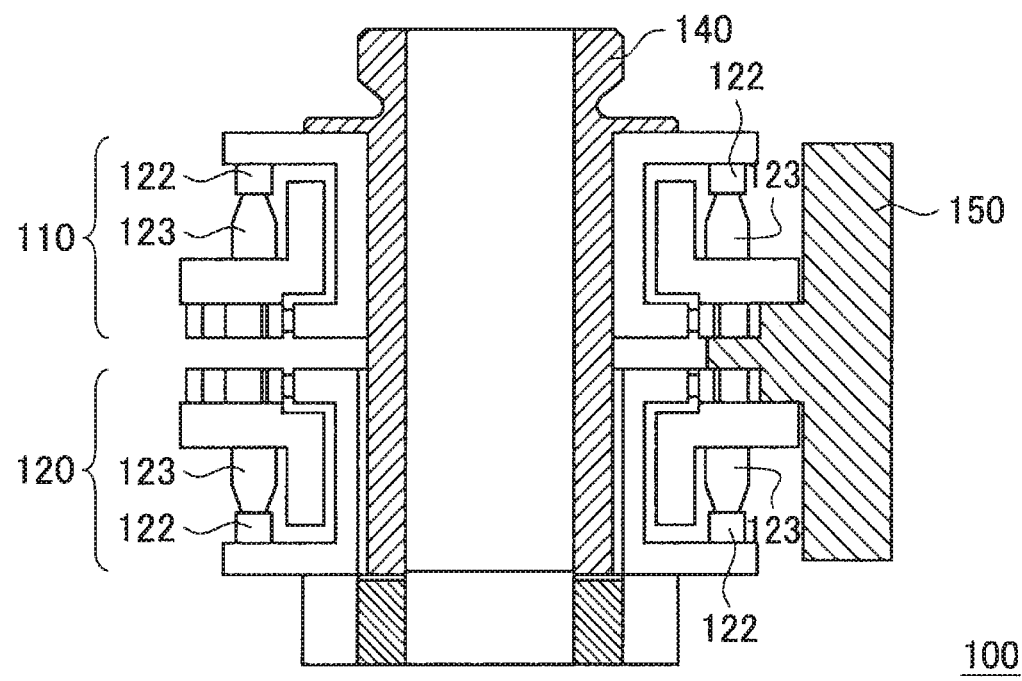
FIG. 4 is a schematic diagram illustrating a state in which, from the configuration illustrated in FIG. 1, only a main configuration related to a medical holding apparatus 100 is illustrated without configurations of a camera head side and an endoscope side.

FIG. 4 is a schematic diagram illustrating a state in which, from the configuration illustrated in FIG. 1, only a main configuration related to the medical holding apparatus 100, except for configurations of the camera head 200 side and the endoscope 300 side, is illustrated. By arbitrarily changing the shape of the frame 150, the frame 150 can be mounted at various medical supporting arm apparatuses 500.

4. Configuration Example of Connecting Location of Camera Head

Figure 5A:
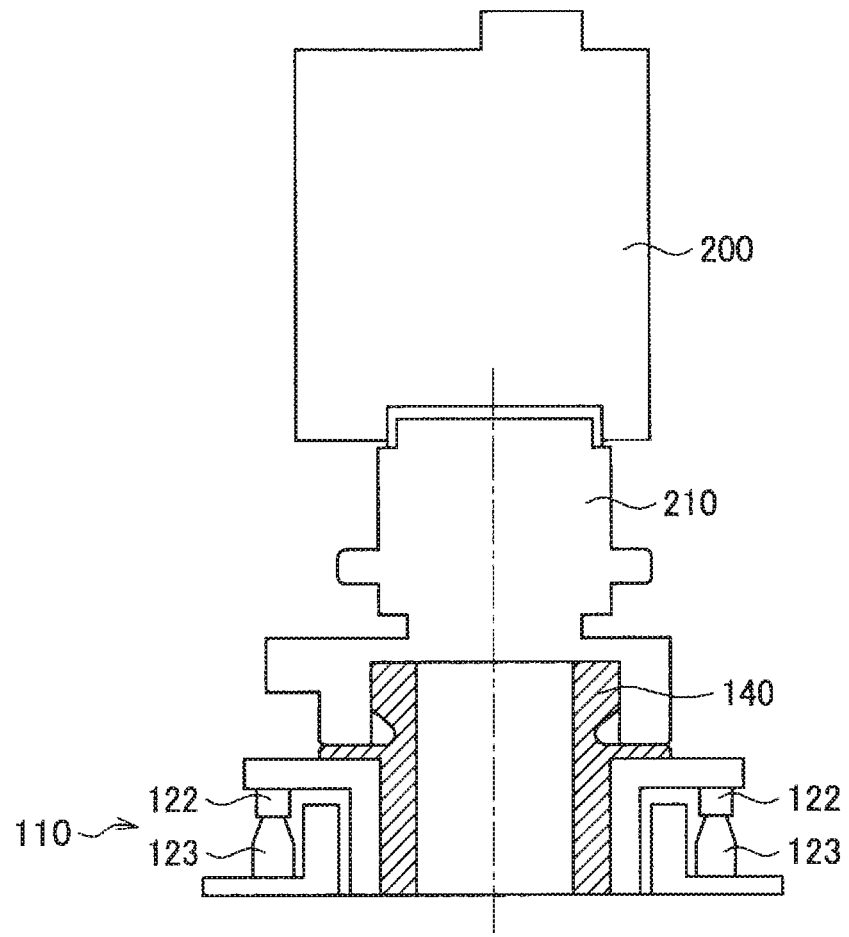
FIG. 5A is a schematic diagram illustrating a specific configuration of a connecting location between the medical holding apparatus and a camera head.
Figure 5B:
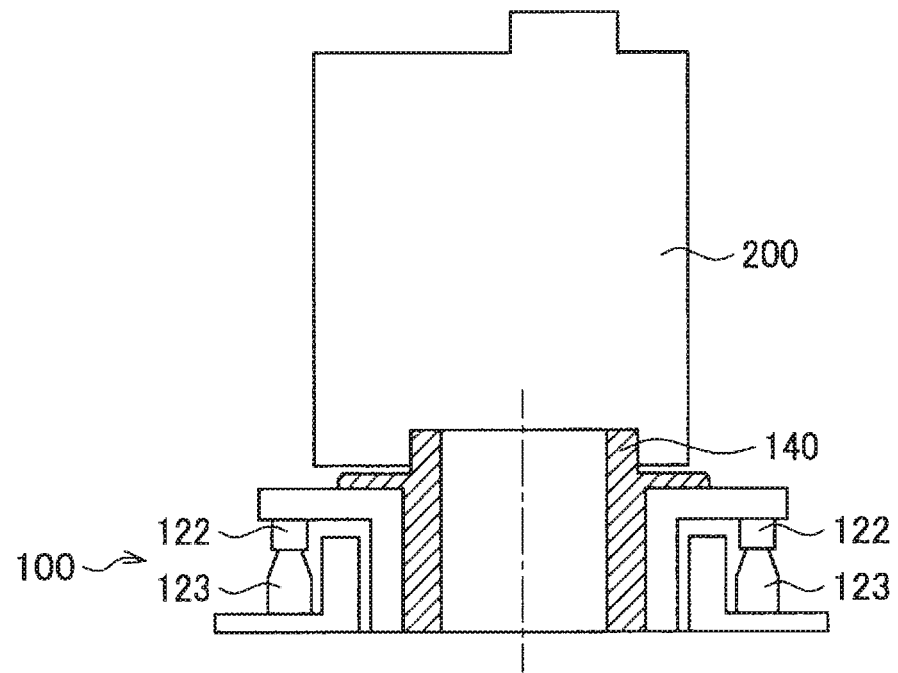
FIG. 5B is a schematic diagram illustrating a specific configuration of a connecting location between the medical holding apparatus and a camera head.

FIGS. 5A and 5B are schematic diagrams illustrating specific configurations of a connecting location between the medical holding apparatus 100 and the camera head 200. FIG. 5A is a schematic diagram illustrating the camera head 200 including the endoscope adaptor 210. Generally, a portion of the endoscope adaptor 210 is directly mounted at the endoscope 300 in the camera head 200 including the endoscope adaptor 210. However, in the present embodiment, since the medical holding apparatus 100 is mounted between the camera head 200 and the endoscope 300, the endoscope adaptor 210 is mounted at the lens barrel 140 of the medical holding apparatus 100. For this reason, a mount unit connectable to the endoscope adaptor 210 is provided at the distal end of the lens barrel 140.

FIG. 5B is a schematic diagram illustrating a case in which a camera head 200 including a screw type C-mount is connected to the medical holding apparatus 100. The camera head 200 including the C-mount is mounted at the lens barrel 140 by screw fastening. For this reason, a male screw of the C-mount is provided at the distal end of the lens barrel 140.

5. Configuration Example of Drape Mounting Mechanism

Figure 6A:
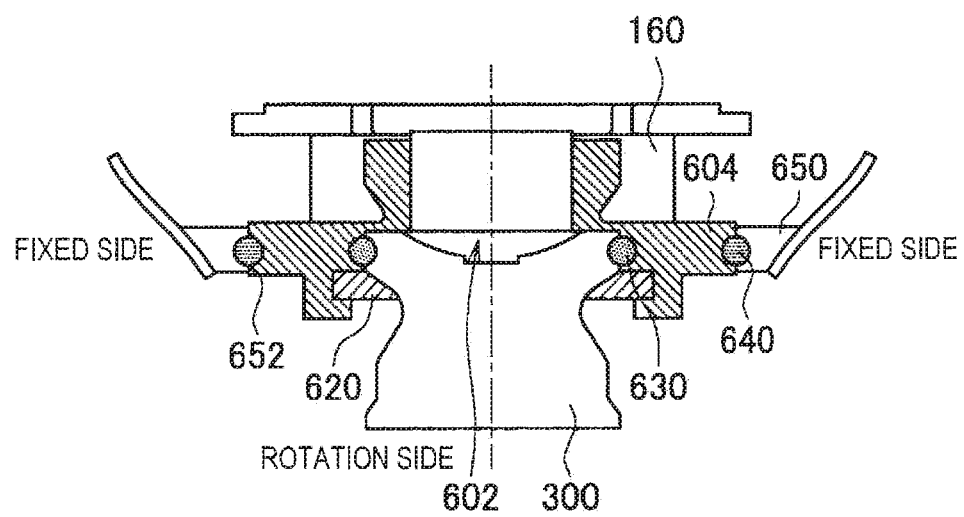
FIG. 6A is a schematic diagram illustrating a configuration of a drape mounting mechanism provided at the endoscope side.

FIG. 6A is a schematic diagram illustrating a configuration of the drape mounting mechanism provided at the endoscope 300 side. In the present embodiment, the drape mounting mechanism includes the rotation mechanism. The adaptor 160 is fixed to the output unit 124 of the actuator 120 at the endoscope 300 side, and the drape mounting unit 600 is mounted at the adaptor 160. A concave portion 602, at which the end of the endoscope 300 at the camera head 200 side is mounted, is provided at the drape mounting unit 600, and a flange 604 is provided at an outer periphery of the drape mounting unit 600. A distal end of the endoscope 300 is inserted into the concave portion 602, and by a plate 620 being inserted into the endoscope 300, the endoscope 300 is connected to the drape mounting unit 600. Consequently, the endoscope 300 integrally rotates with the drape mounting unit 600. An O-ring 630 for preventing liquid intrusion is inserted between the concave portion 602 and the distal end of the endoscope 300.

An outer periphery of the flange 604 is mounted in a hole 652, which is provided in a fixing member 650, through an O-ring 640. To prevent liquid intrusion, the O-ring 640 is provided to cause the flange 604 of the drape mounting unit 600 to slide relative to the fixing member 650. The fixing member 650 is, for example, connected to the frame 150 of the medical holding apparatus 100 and does not rotate together with the camera head 200 or the endoscope 300.

With the above-described configuration, by driving the actuator 120 provided at the endoscope 300 side, the adaptor 160 rotates relative to the frame 150, and the drape mounting unit 600 and the endoscope 300 rotate together with the adaptor 160. On the other hand, the fixing member 650 is fixed without rotating. At this time, since the O-ring 640 for sliding is provided between the drape mounting unit 600 and the fixing member 650, the drape mounting unit 600 rotates while sliding relative to the fixing member 650. Due to the O-ring 640 being provided, when the drape mounting unit 600 is rotated relative to the fixing member 650, liquid intrusion from between the fixing member 650 and the drape mounting unit 600 may be suppressed.

Figure 6B:
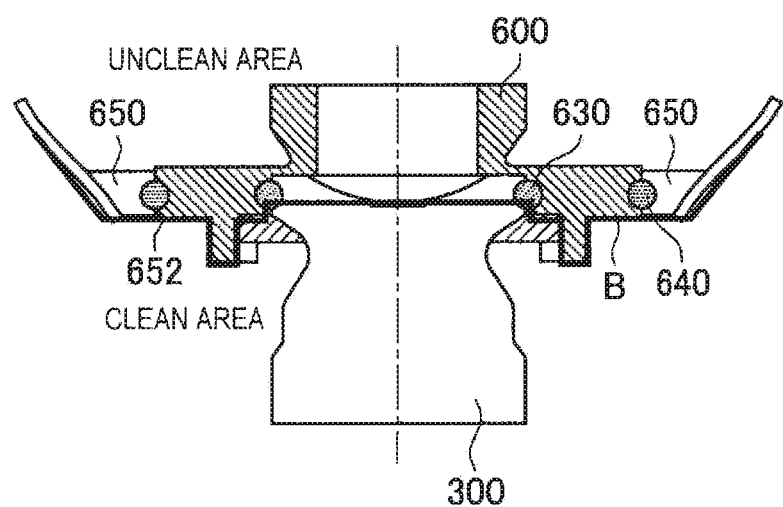
FIG. 6B is a schematic diagram illustrating a state in which separation between a clean area and an unclean area has been performed with the drape mounting mechanism as a boundary.

Therefore, the drape mounting unit 600 has a mechanism that is rotatable relative to the fixing member 650 and blocks intrusion of liquid or the like into the medical holding apparatus 100 side. Consequently, as illustrated in FIG. 6B, separation between a clean area and an unclean area can be performed with the drape mounting unit 600 as a boundary. In FIG. 6B, the clean area and the unclean area are separated with a boundary B indicated by a thick line.

Since the endoscope 300 is connected to the drape mounting unit 600 through the O-ring 630, liquid intrusion from a clearance between the endoscope 300 and the drape mounting unit 600 may also be suppressed.

Although an example in which the O-ring 640 is caused to slide in order for the drape mounting unit 600 to be a rotatable mechanism is illustrated in FIG. 6, a closed type bearing may be used instead of the O-ring 640. The drape mounting unit 600 may also be caused to directly slide relative to the fixing member 650 as long as liquid intrusion can be prevented using, for example, an oil film or the like.

6. Connecting Structure to Arm Side

Figure 7A:
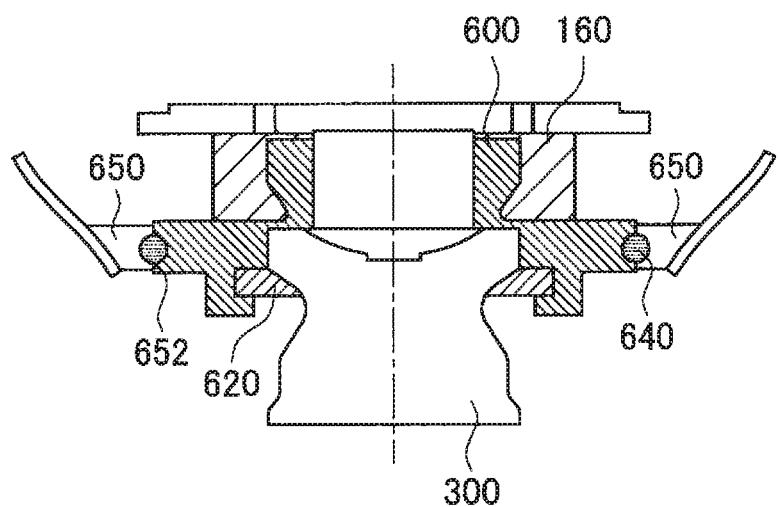
FIG. 7A is a schematic cross-sectional diagram illustrating an example of a method of connecting the drape mounting mechanism and the medical holding apparatus.
Figure 7B:
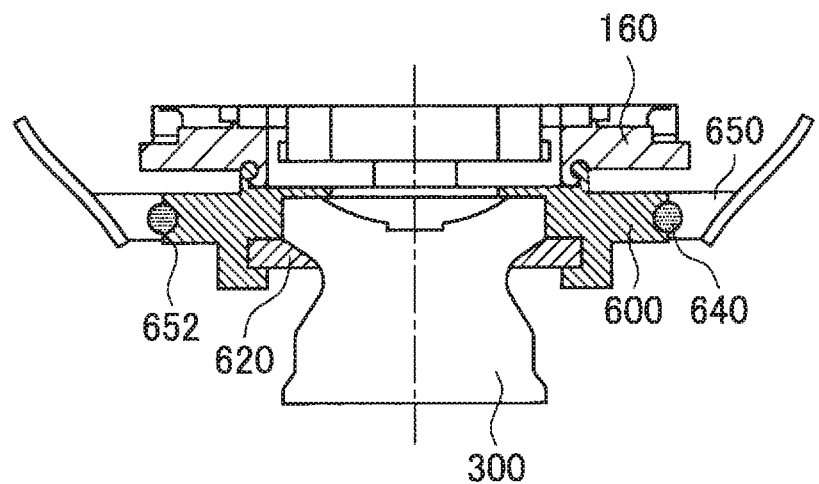
FIG. 7B is a schematic cross-sectional diagram illustrating an example of a method of connecting the drape mounting mechanism and the medical holding apparatus.

FIGS. 7A and 7B are schematic cross-sectional diagrams illustrating an example of a method of connecting the drape mounting unit 600 and the medical holding apparatus 100. FIG. 7A illustrates a case in which the drape mounting unit 600 is made connectable to a versatile endoscope. FIG. 7B illustrates a case in which the drape mounting unit 600 is designed exclusively for the medical holding apparatus 100.

In the case of the configuration illustrated in FIG. 7A, the connection between the adaptor 160 and the drape mounting unit 600 is performed in the same manner as a ready-made article with versatility. Therefore, in a case in which the drape mounting unit 600 is not in use, it becomes possible to directly mount the endoscope 300 at the adaptor 160. In other words, a connecting structure of the drape mounting unit 600 to the adaptor 160 and a connecting structure of the endoscope 300 to the drape mounting unit 600 are the same.

On the other hand, in the case of the configuration illustrated in FIG. 7B, since the drape mounting unit 600 is exclusively designed for the medical holding apparatus 100, thicknesses of the drape mounting unit 600 and the adaptor 160 in an optical axis direction can be made sufficiently thin, and thus further miniaturization can be achieved.

7. Fixing Structure of Endoscope

Figure 8:
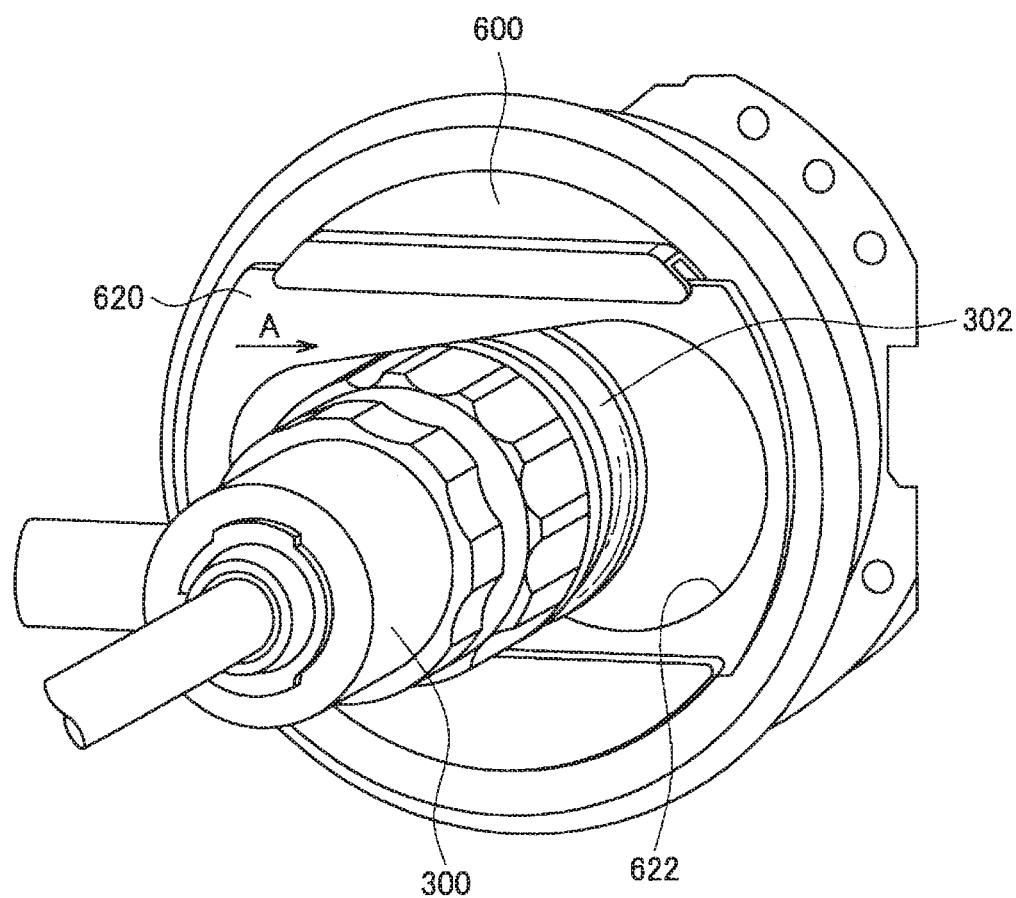
FIG. 8 is a schematic diagram illustrating a structure for fixing an endoscope.

FIG. 8 is a schematic diagram illustrating a structure for fixing an endoscope 300. Various methods are already known regarding a method of fixing the endoscope 300, and the method is not particularly limited. FIG. 8 illustrates a method of fixing the endoscope 300 using the plate 620 illustrated in FIG. 6 and the like. A long hole 622 corresponding to a flange 302 at the distal end of the endoscope 300 is provided in the plate 620, and a width of the long hole 622 in a vertical direction in FIG. 8 varies in accordance with a position thereof in a horizontal direction. More specifically, the width of the long hole 622 in the vertical direction progressively narrows toward the left in FIG. 8. By inserting the flange 302 into the long hole 622 and causing the plate 620 to slide in a direction indicated by an arrow A, an edge of the long hole 622 is engaged with the flange 302, and the endoscope 300 can be fixed to the drape mounting unit 600.

Figure 9A:
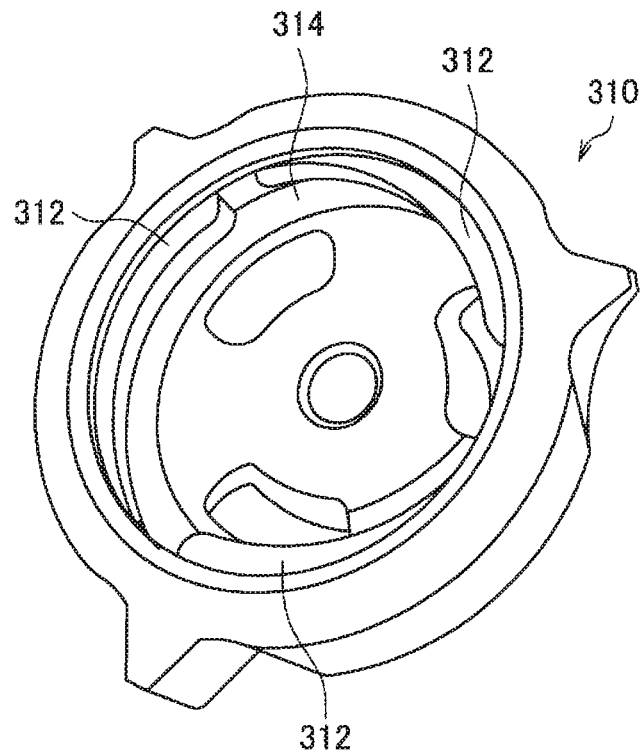
FIG. 9A is a schematic diagram illustrating an example of a cam mechanism, which is a mechanism of a detachable unit of a general endoscope.
Figure 9B:
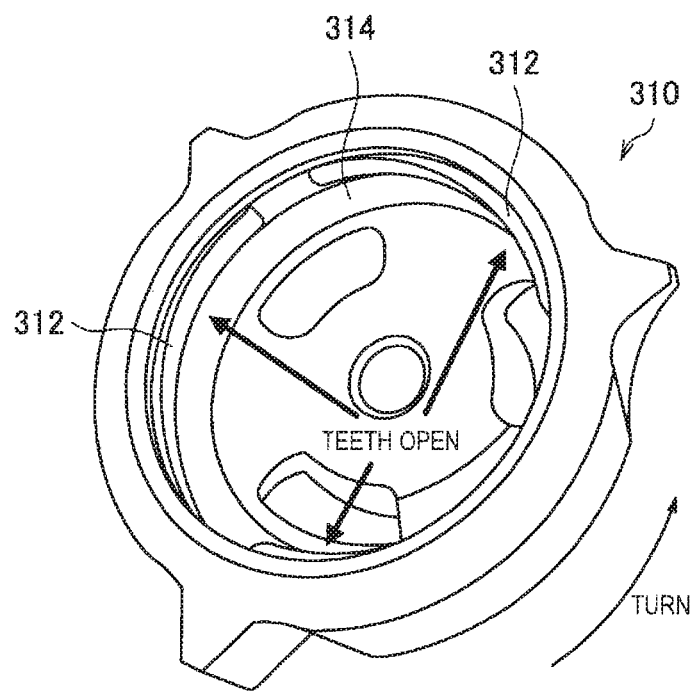
FIG. 9B is a schematic diagram illustrating an example of a cam mechanism, which is a mechanism of a detachable unit of a general endoscope.
Figure 9C:
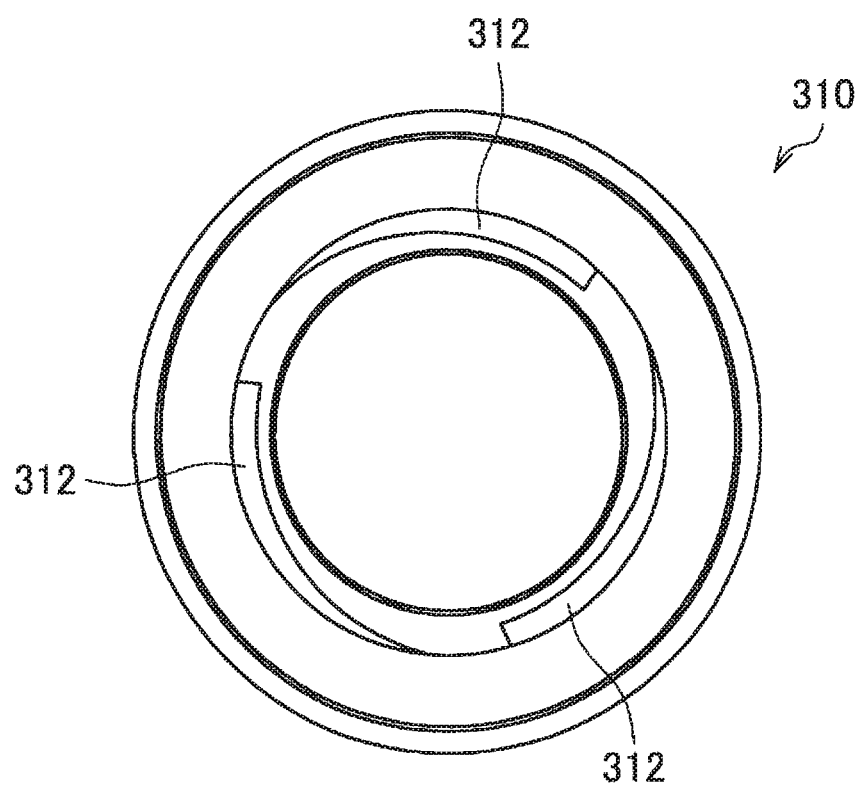
FIG. 9C is a schematic diagram illustrating an example of a cam mechanism, which is a mechanism of a detachable unit of a general endoscope.

FIGS. 9A, 9B, and 9C are schematic diagrams illustrating examples of a cam mechanism, which is a mechanism of a detachable unit 310 of a general endoscope. In the above-described connection between the medical holding apparatus 100 and the drape mounting unit 600 and connection between the medical holding apparatus 100 and the endoscope 300, one-touch detachment can be realized by using a cam mechanism. In FIG. 9A, a rib 312 protrudes from an inner periphery of the detachable unit 310. When, as illustrated in FIG. 9B, the rib 312 rotates about an outer periphery of the detachable unit 310 from the state illustrated in FIG. 9A, the rib 312 retracts outward. Therefore, by causing a flange of a mating member, which is mounted at the detachable unit 310, to be engaged between the rib 312 and an inner wall surface 314 of the rib 312 in the state illustrated in FIG. 9A, the mating member and the detachable unit 310 are connected. On the other hand, when the rib 312 is caused to retract outward in the state illustrated in FIG. 9B, the engagement between the rib 312 and the flange of the mating member is disengaged, and the detachable unit 310 can be detached from the mating member.

FIG. 9C illustrates a state in which the rib 312 protrudes inward. A mechanism for driving the rib 312 can be realized by a general method such as providing a cam, which rotates together with rotation of the outer periphery of the detachable unit 310, and causing a cam follower provided at the rib 312 to be engaged with the cam. The mechanism of the detachable unit 310 can be applied not only to a connection unit between the endoscope 300 and the medical holding apparatus 100 but also to a connection unit between the camera head 200 and the medical holding apparatus 100.

8. Example of Specific Control Using Medical Holding Apparatus

By simultaneous control of the two actuators in accordance with a joint angle and a joint torque, in the present embodiment, control can be performed in three modes, including an all-free operation mode, a scope fixing-camera head rotating operation mode, and a camera head fixing-scope rotating operation mode, as oblique viewing endoscope operation modes.

8.1. All-Free Operation Mode

In the all-free operation mode, an endoscope gripping arm is directly operated by hand in a state close to a no-load state to enable free field-of-view development. A method of realizing the no-load state in the all-free mode varies in accordance with a type of mounted actuator. In a case in which a torque sensorless ultrasonic motor is mounted at a joint of the medical supporting arm apparatus 500, by phase difference zero control under a driving voltage application state, a friction and a starting torque between a stator and a rotor are minimized such that the no-load state is realized. In a case in which a force control type actuator with a torque sensor is mounted at each joint, the no-load state is realized by zero torque control in which control of rotation of an actuator is performed in a direction in which an external force detected by the torque sensor is cancelled. In the medical holding apparatus 100, the no-load state by the all-free operation mode is realized by performing the phase difference zero control in a state in which a driving voltage is applied to the ultrasonic motor mounted at the actuators 110 and 120.

Figure 10:
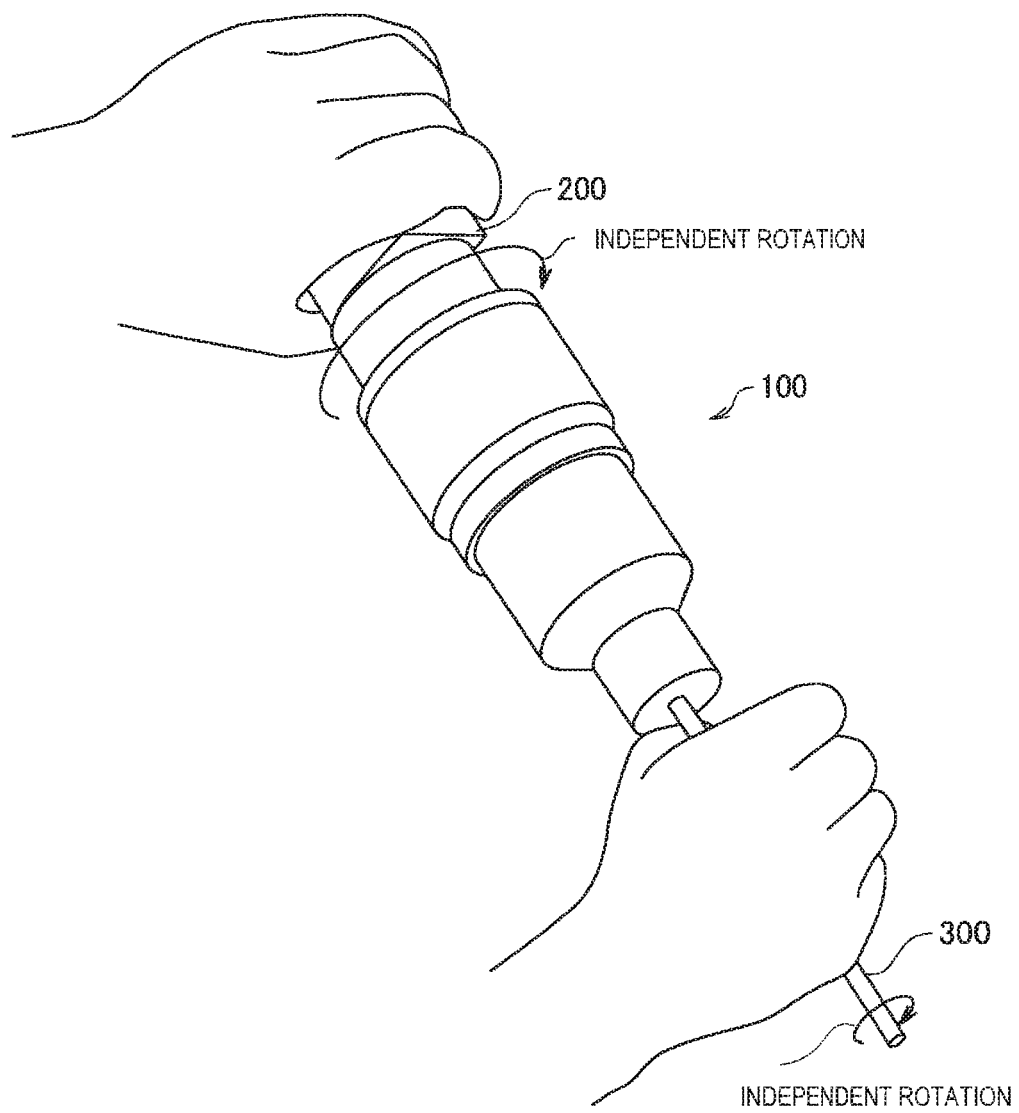
FIG. 10 is a schematic diagram illustrating a camera head-scope non-interlocking all-free mode.
Figure 11:
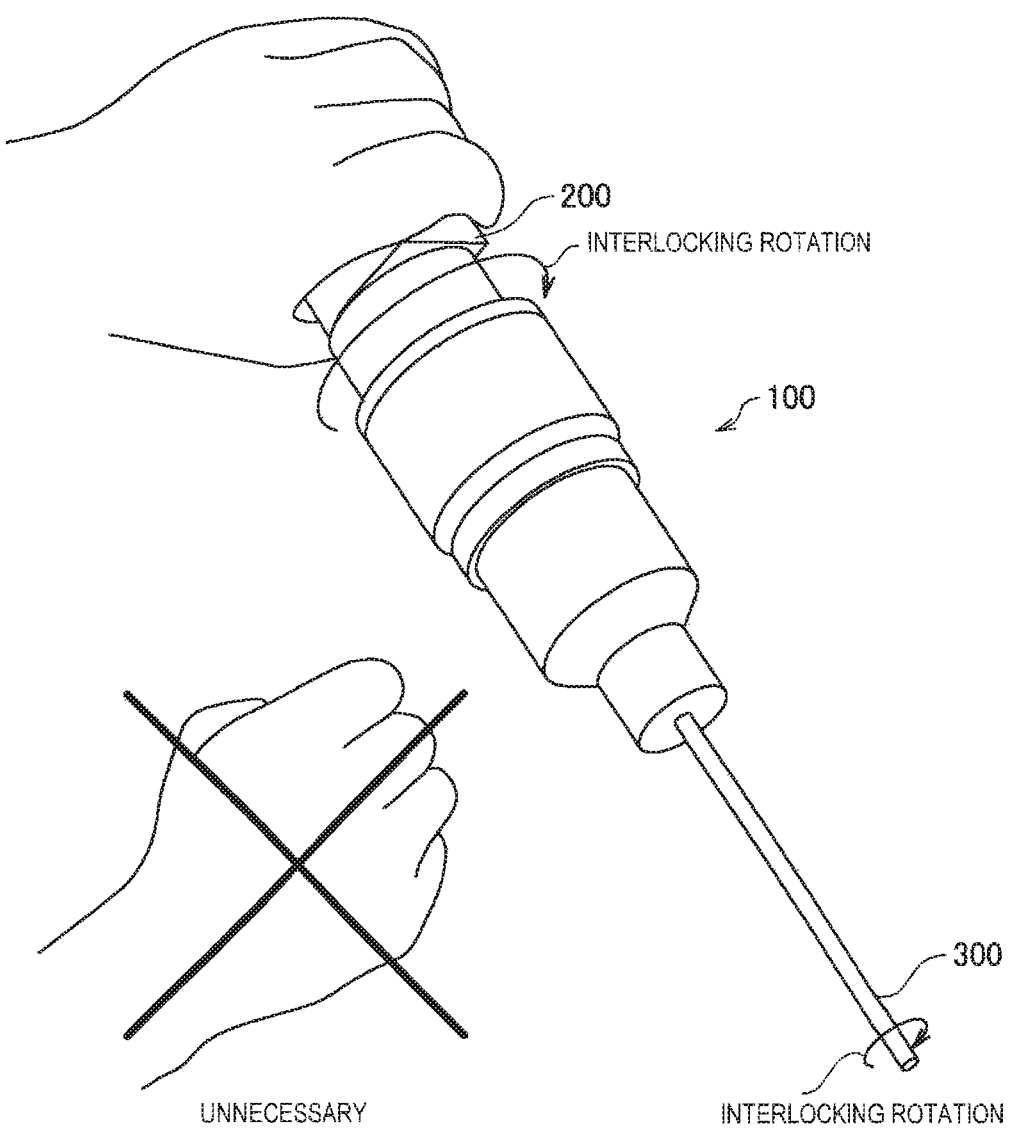
FIG. 11 is a schematic diagram illustrating a camera head-scope interlocking all-free mode.
Figure 12:
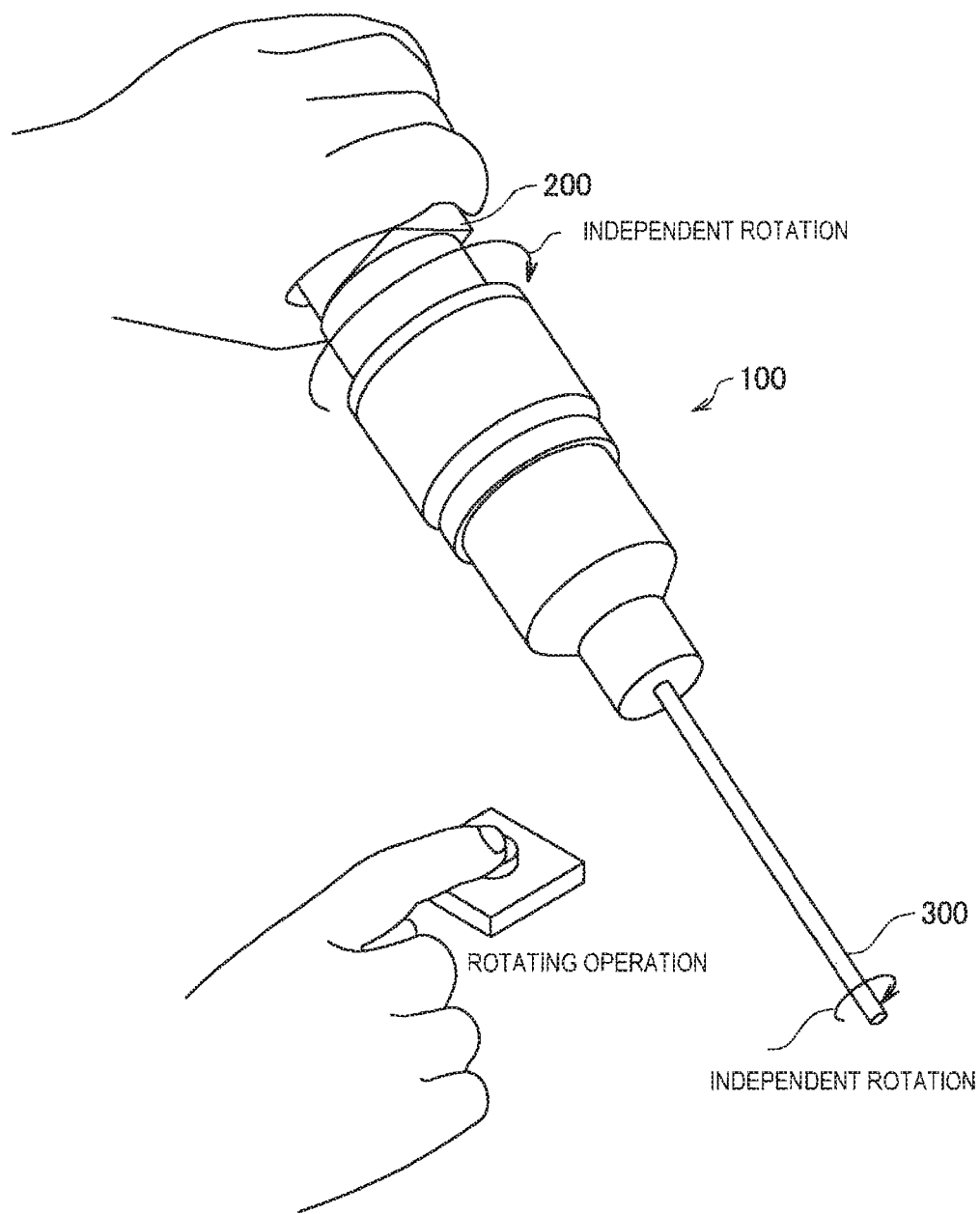
FIG. 12 is a schematic diagram illustrating a combination of a scope rotation control mode and a camera head all-free mode.

In the present embodiment, by switching an interlocking control method of the two actuators 110 and 120 in the all-free operation mode, the all free operation mode corresponds to the three types of direct operation variations illustrated in FIGS. 10 to 12.

FIG. 10 is a schematic diagram illustrating a camera head-scope non-interlocking all-free mode. In this mode, by performing the control by the all-free operation mode independently of a rotation axis of the camera head 200 and a rotation axis of the endoscope 300, a simultaneous positioning operation of a position of the camera head 200 and a position of the endoscope 300 becomes possible by direct operation using both hands. By controlling a phase difference zero of each of the two actuators 110 and 120 in the driving voltage application state, it is possible to operate each of the camera head 200 and the endoscope 300 by hand. Both the rotation axis of the camera head 200 and the rotation axis of the endoscope 300 are in the no-load state.

FIG. 11 is a schematic diagram illustrating a camera head-scope interlocking all-free mode. In this mode, by performing control by the all-free operation mode on the rotation axis of the camera head 200, interlocking position control in accordance with a rotational angle of the camera head 200 is performed on the rotation axis of the endoscope 300. Consequently, a direct rotation operation of the camera head 200 and the endoscope 300 becomes possible with only a one-hand gripping operation of the camera head 200. In this case, the camera head 200 can be controlled in the all-free operation mode by controlling a phase difference zero of the actuator 110 in the driving voltage application state. At this time, since a rotational angle of the actuator 110 can be detected by an encoder of the actuator 110, the actuator 110 for driving the endoscope 300 is driven in accordance with the rotational angle of the actuator 110. Consequently, movement of the endoscope 300 can be interlocked with movement of the camera head 200 by the all-free operation mode. The rotation axis of the camera head 200 is set as a no-load axis, and the rotation axis of the endoscope 300 is interlocked with the camera head 200.

FIG. 12 is a schematic diagram illustrating a combination of a scope rotation control mode and a camera head all-free mode. In this mode, all-free control is performed on the rotation axis of the camera head 200, and the rotation axis of the endoscope 300 realizes independent position control through a rotation operation of another input device. For example, rotation of the endoscope 300 is controlled on the basis of an indicated value that is input to an input unit 359 of a controlling apparatus 350 which will be described below. The input unit 359 corresponds to an input device. The rotation axis of the camera head 200 is set as a no-load axis, and the rotation axis of the endoscope 300 rotates independently of the camera head 200.

8.2. Scope Fixing-Camera Head Rotating Operation Mode

The scope fixing-camera head rotating operation mode enables rotation of the camera head 200 in a state in which a field of view of the endoscope 300 is maintained, after positioning of the medical supporting arm apparatus 500. The scope fixing-camera head rotating operation mode is realized by position fixing control of the rotation axis of the endoscope 300 and control of the rotation axis of the camera head 200 in accordance with the type of actuator and each of the following modes. In any of the following modes, rotation of the endoscope 300 is fixed. The fixation of rotation of the endoscope 300 can be performed by stopping energization to the actuator 120 including an ultrasonic motor. The scope fixing-camera head rotating operation mode corresponds to two types of rotational operation variations with different ways for realizing rotation of the camera head 200.

Figure 13:
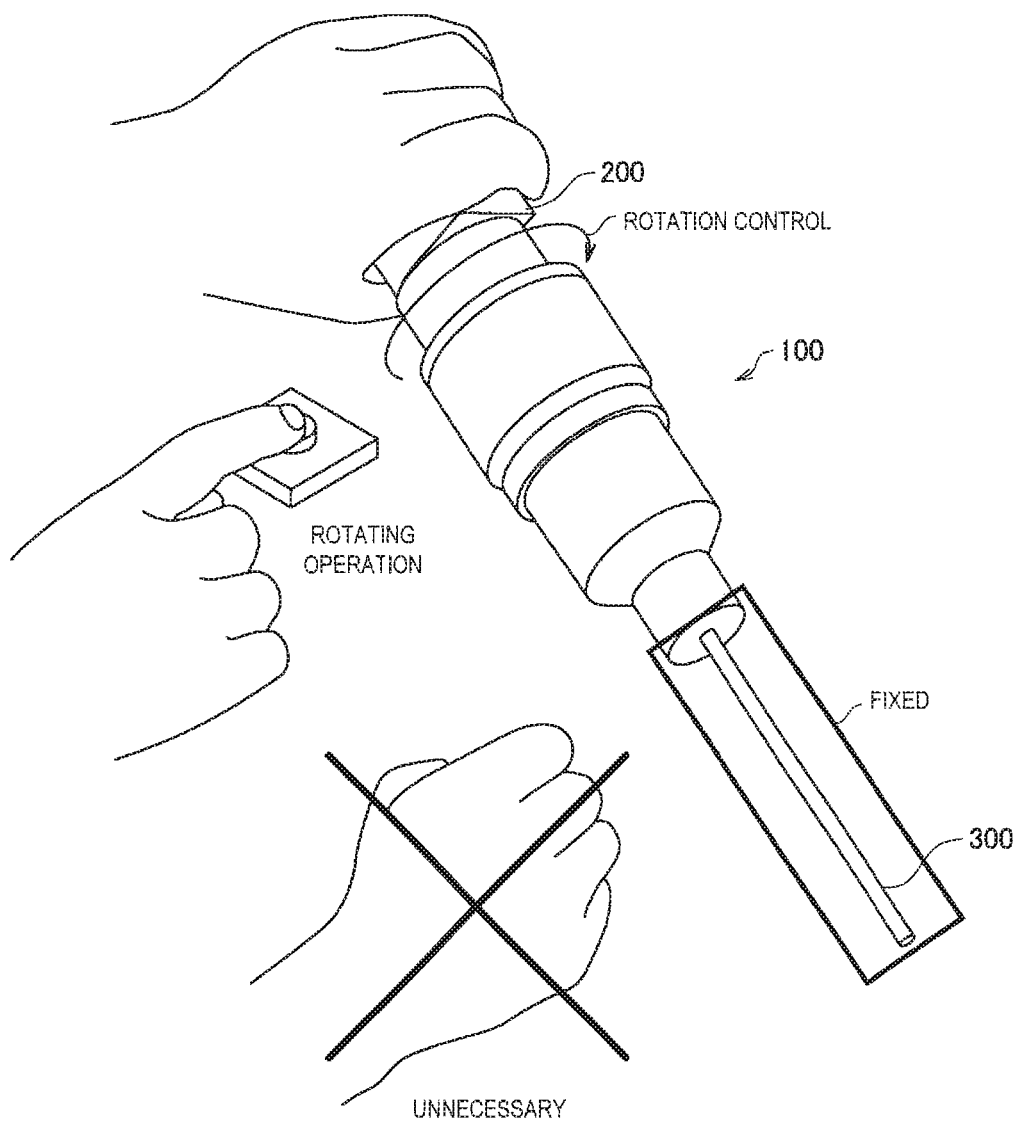
FIG. 13 is a schematic diagram illustrating a camera head rotation control mode.

FIG. 13 is a schematic diagram illustrating a camera head rotation control mode. In this mode, rotation of the camera head 200 is realized by a direct operation by the all-free control with respect to the rotation axis of the camera head 200 or a rotation operation by another input device. The rotation axis of the camera head 200 is rotation-controlled by no load or an input device, and the rotation axis of the endoscope 300 is fixed.

Figure 14:
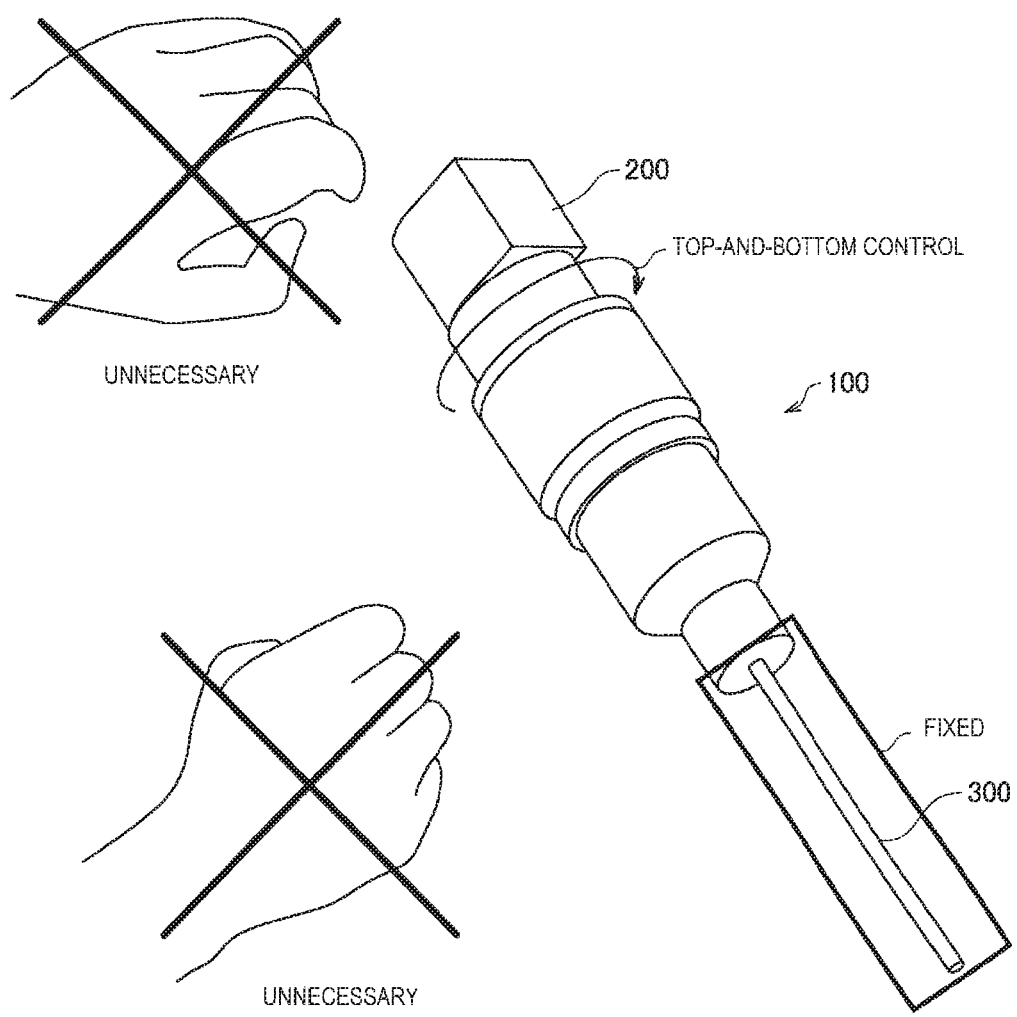
FIG. 14 is a schematic diagram illustrating a camera head top-and-bottom control mode.

FIG. 14 is a schematic diagram illustrating a camera head top-and-bottom control mode. In this mode, the camera head 200 is rotated in a top-and-bottom direction, which is calculated from an angle of the rotation axis of the camera head 200 and an arm attitude. During the camera head top-and-bottom control mode, a rotation operation by an operator (a surgeon or surgery support staff) is not necessary. By calculating the direction of gravity from an attitude of the medical supporting arm apparatus 500, the rotation axis of the camera head 200 rotates the camera head 200 so that the camera head 200 follows the direction of gravity. The rotation axis of the endoscope 300 is fixed. The direction of gravity may be calculated not only from the attitude of the medical supporting arm apparatus 500 but also from a sensor such as a gyro sensor.

8.3. Camera Head Fixing-Scope Rotating Operation Mode

The camera head fixing-scope rotating operation mode enables field-of-view development only in a rotating direction of the endoscope 300 in a state in which a position of the camera head 200 is maintained, after positioning of the medical supporting arm apparatus 500. The camera head fixing-scope rotating operation mode is realized by position fixing control of the rotation axis of the camera head 200 and control of the rotation axis of the endoscope 300 in accordance with the type of actuator and an operation way. In the camera head fixing-scope rotating operation mode, rotation of the camera head 200 is fixed. The fixation of rotation of the camera head 200 can be performed by stopping energization to the actuator 110 including an ultrasonic motor.

Figure 15:
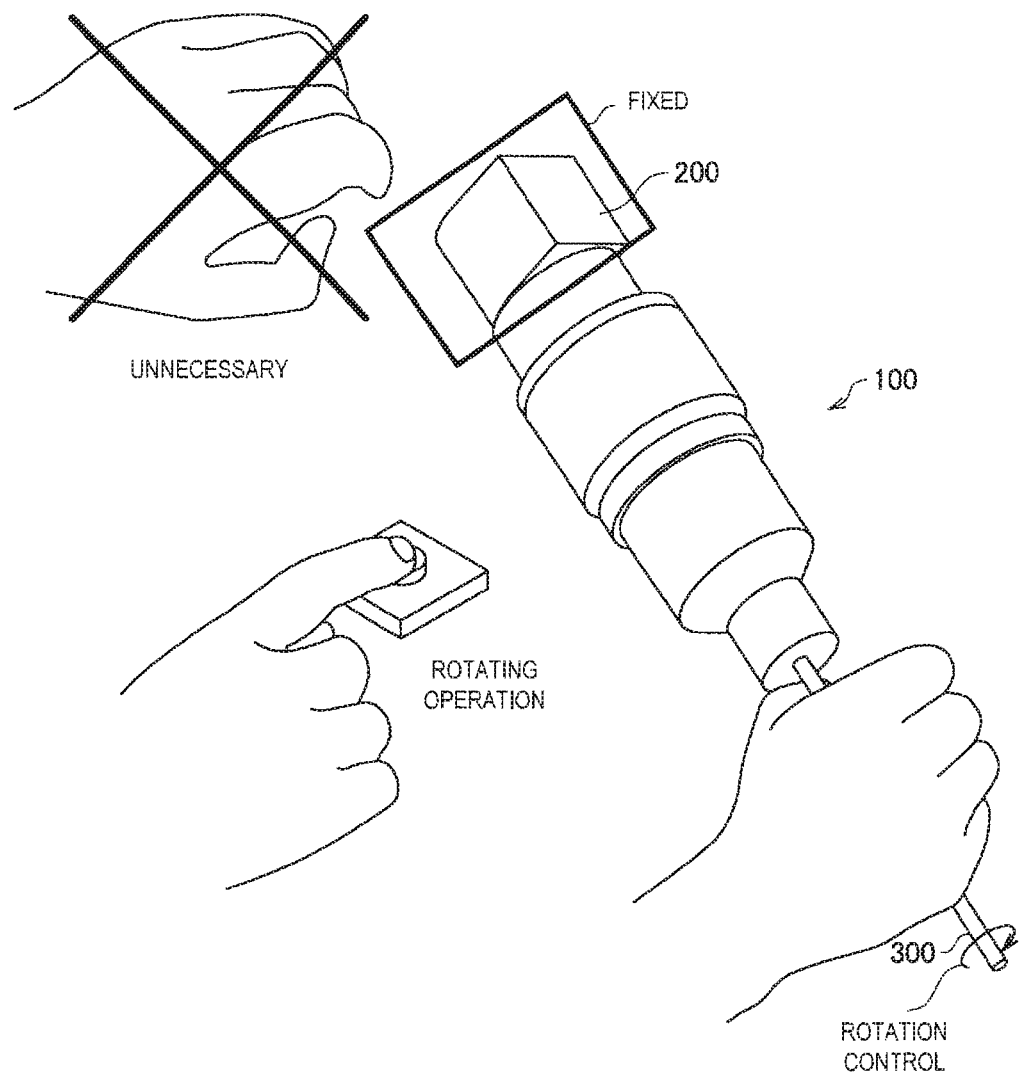
FIG. 15 is a schematic diagram illustrating the scope rotation control mode.

FIG. 15 is a schematic diagram illustrating the scope rotation control mode. In this mode, rotation of the endoscope 300 is realized by a direct operation by the all-free control with respect to the rotation axis of the endoscope 300 or a rotation operation by another input device.

9. Application Examples

The technology according to an embodiment of the present disclosure can be applied to various products. For example, the technology according to an embodiment of the present disclosure may be applied to an endoscopic surgery system. The supporting arm apparatus 5027 which will be described below corresponds to the medical supporting arm apparatus 500 illustrated in FIG. 1.

Figure 16:
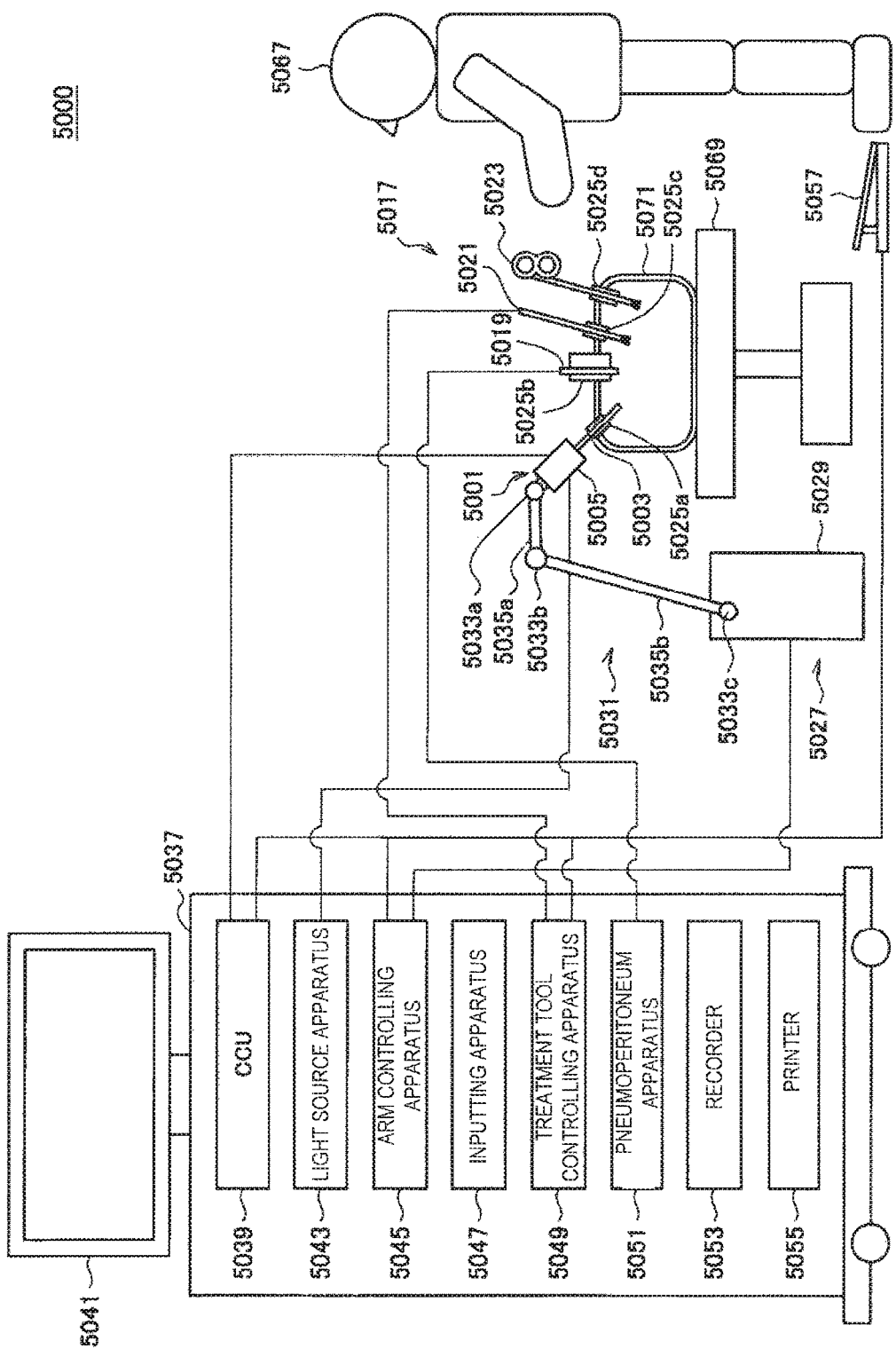
FIG. 16 is a view depicting an example of a schematic configuration of an endoscopic surgery system.

FIG. 16 is a view depicting an example of a schematic configuration of an endoscopic surgery system 5000 to which the technology according to an embodiment of the present disclosure can be applied. In FIG. 16, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d are used to puncture the abdominal wall. Then, a lens barrel 5003 of the endoscope 5001 and the other surgical tools 5017 are inserted into body lumens of the patient 5071 through the trocars 5025a to 5025d. In the example depicted, as the other surgical tools 5017, a pneumoperitoneum tube 5019, an energy treatment tool 5021 and forceps 5023 are inserted into body lumens of the patient 5071. Further, the energy treatment tool 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, a pair of tweezers or a retractor may be used.

An image of a surgical region in a body lumen of the patient 5071 imaged by the endoscope 5001 is displayed on a display apparatus 5041. The surgeon 5067 would use the energy treatment tool 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy treatment tool 5021 and the forceps 5023 are supported by the surgeon 5067, an assistant or the like during surgery.

(Supporting Arm Apparatus)

The supporting arm apparatus 5027 includes an arm unit 5031 extending from a base unit 5029. In the example depicted, the arm unit 5031 includes joint portions 5033a, 5033b and 5033c and links 5035a and 5035b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body lumen of the patient 5071, and a camera head 5005 connected to a proximal end of the lens barrel 5003. In the example depicted, the endoscope 5001 is depicted which includes as a rigid endoscope having the lens barrel 5003 of the hard type. However, the endoscope 5001 may otherwise be configured as a flexible endoscope having the lens barrel 5003 of the soft type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body lumen of the patient 5071 through the objective lens. It is to be noted that the endoscope 5001 may be a forward viewing endoscope or may be an oblique viewing endoscope or a side viewing endoscope.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy treatment tool 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone. By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy treatment tool 5021 for cautery or incision of a tissue, sealing of a blood vessel or the like. A pneumoperitoneum apparatus 5051 feeds gas into a body lumen of the patient 5071 through the pneumoperitoneum tube 5019 to inflate the body lumen in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033a, 5033b and 5033c and the plurality of links 5035a and 5035b connected to each other by the joint portion 5033b. In FIG. 16, for simplified illustration, the configuration of the arm unit 5031 is depicted in a simplified form. Actually, the shape, number and arrangement of the joint portions 5033a to 5033c and the links 5035a and 5035b and the direction and so forth of axes of rotation of the joint portions 5033a to 5033c can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body lumen of the patient 5071.

An actuator is provided in each of the joint portions 5033a to 5033c, and the joint portions 5033a to 5033c are configured such that they are rotatable around predetermined axes of rotation thereof by driving of the respective actuators. The driving of the actuators is controlled by the arm controlling apparatus 5045 to control the rotational angle of each of the joint portions 5033a to 5033c thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endoscope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the surgery room.

Further, where force control is applied, the arm controlling apparatus 5045 may perform power-assisted control to drive the actuators of the joint portions 5033a to 5033c such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033*a* to 5033*c* of the arm unit 5031 of the supporting arm apparatus 5027 such that the plurality of arm controlling apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. In special light observation, for example, by utilizing the wavelength dependency of absorption of light in a body tissue to irradiate light of a narrower band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrowband light and/or excitation light suitable for special light observation as described above.

(Camera Head and CCU)

Figure 17:
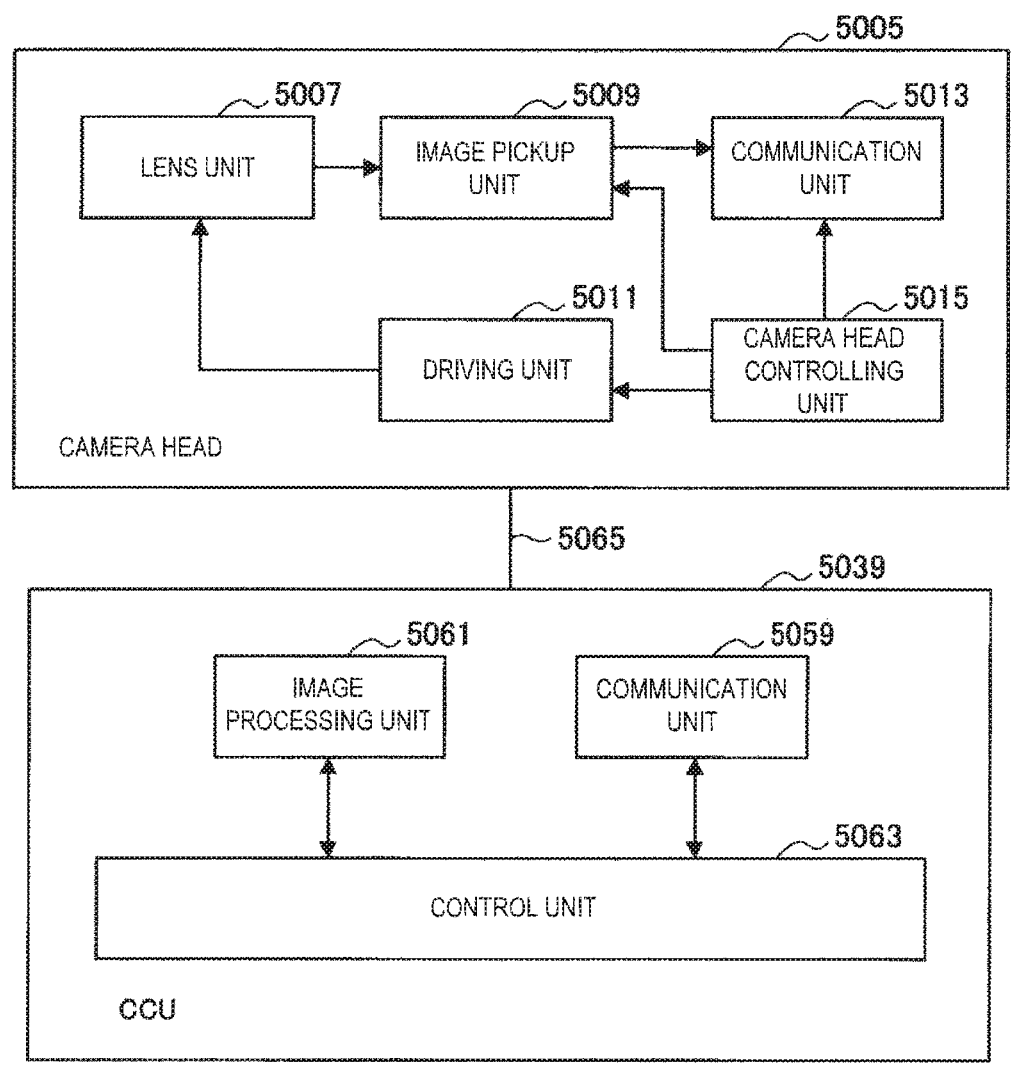
FIG. 17 is a block diagram depicting an example of a functional configuration of a camera head and a camera control unit (CCU) depicted in FIG. 16.

Functions of the camera head 5005 of the endoscope 5001 and the CCU 5039 are described in more detail with reference to FIG. 17. FIG. 17 is a block diagram depicting an example of a functional configuration of the camera head 5005 and the CCU 5039 depicted in FIG. 16.

Referring to FIG. 17, the camera head 5005 has, as functions thereof, a lens unit 5007, an, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy treatment tool 5021 is used and so forth by detecting the shape, color and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the surgery room. Therefore, such a situation that movement of medical staff in the surgery room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a soft endoscopic system for inspection or a microscopic surgery system.

10. Specific Configuration Example of Medical Supporting Arm Apparatus

Next, a specific configuration example of a medical supporting arm apparatus according to an embodiment of the present disclosure will be described in detail. The supporting arm apparatus which will be described below is an example in which the supporting arm apparatus is configured as a supporting arm apparatus configured to support an endoscope at a distal end of an arm unit, but the present embodiment is not limited to such an example.

Figure 18:
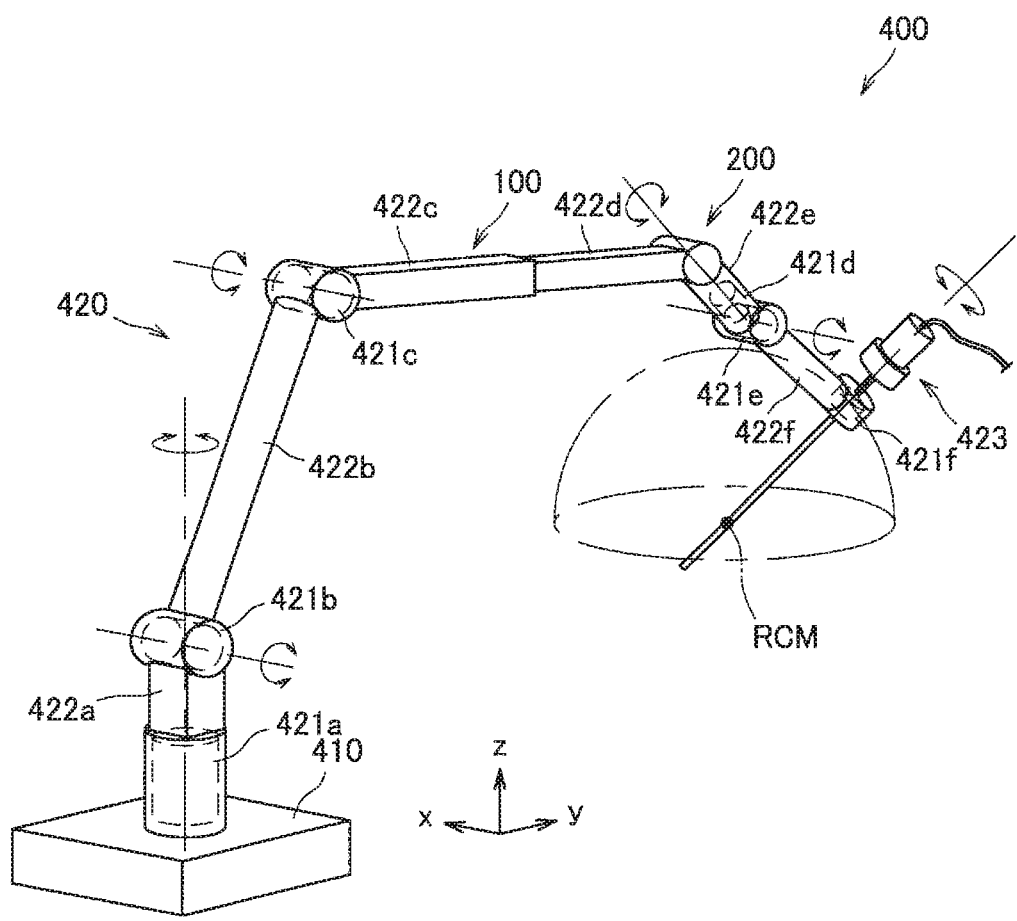
FIG. 18 is a perspective diagram illustrating a configuration example of a medical supporting arm apparatus according to an embodiment of the present disclosure.

First, a schematic configuration of a supporting arm apparatus 400 according to the present embodiment will be described with reference to FIG. 18. FIG. 18 is a schematic diagram illustrating an exterior of the supporting arm apparatus 400 according to the present embodiment.

The supporting arm apparatus 400 according to the present embodiment includes a base unit 410 and an arm unit 420. The base unit 410 is a base of the supporting arm apparatus 400, and the arm unit 420 extends from the base unit 410. Although not illustrated in FIG. 18, a control unit configured to integrally control the supporting arm apparatus 400 may be provided in the base unit 410, and driving of the arm unit 420 may be controlled by the control unit. The control unit is constituted by various signal processing circuits such as a central processing unit (CPU) or a digital signal processor (DSP).

The arm unit 420 has a plurality of active joint portions 421a to 421f, a plurality of links 422a to 422f, and an endoscope apparatus 423 as a distal end unit provided at a distal end of the arm unit 420.

The links 422a to 422f are substantially bar-like members. One end of the link 422a is connected to the base unit 410 through the active joint portion 421a, the other end of the link 422a is connected to one end of the link 422b through the active joint portion 421b, and the other end of the link 422b is connected to one end of the link 422c through the active joint portion 421c. The other end of the link 422c is connected to the link 422d through a passive sliding mechanism 100, and the other end of the link 422d is connected to one end of the link 422e through a passive joint portion 200. The other end of the link 422e is connected to one end of the link 422f through the active joint portions 421d and 421e. The endoscope apparatus 423 is connected to the distal end of the arm unit 420, that is, the other end of the link 422f, through the active joint portion 421f. By the ends of the plurality of links 422a to 422f being connected to each other by the active joint portions 421a to 421f, the passive sliding mechanism 100, and the passive joint portion 200 with the base unit 410 as a fulcrum as described above, a shape of an arm extending from the base unit 410 is configured.

A position and attitude of the endoscope apparatus 423 are controlled by actuators, which are respectively provided at the active joint portions 421a to 421f of the arm unit 420, being drive-controlled. In the present embodiment, the distal end of the endoscope apparatus 423 enters a body cavity of a patient, which is a treatment site, and images a partial region of the treatment site. However, the distal end unit provided at the distal end of the arm unit 420 is not limited to the endoscope apparatus 423, and various other medical mechanisms may be connected to the distal end of the arm unit 420 as the distal end unit. As described above, the supporting arm apparatus 400 according to the present embodiment is configured as a medical supporting arm apparatus including a medical mechanism.

Here, in the following description, the supporting arm apparatus 400 will be described by defining coordinate axes as illustrated in FIG. 18. Also, a vertical direction, a longitudinal direction, and a horizontal direction are defined in accordance with the coordinate aces. That is, a vertical direction with respect to the base unit 410 provided at a floor surface is defined as the z-axis direction and the vertical direction. Also, a direction in which the arm unit 420 extends from the base unit 410 (that is, a direction in which the endoscope apparatus 423 is positioned with respect to the base unit 410), which is a direction orthogonal to the z-axis, is defined as the y-axis direction and the longitudinal direction. Further, a direction orthogonal to the y-axis and the z-axis is defined as the x-axis direction and the horizontal direction.

The active joint portions 421a to 421f connect the links to each other such that the links are rotatable. The active joint portions 421a to 421f have an actuator and a rotation mechanism that is rotation-driven with respect to a predetermined rotation axis by driving of the actuator. By separately controlling rotation-driving of each of the active joint portions 421a to 421f, it is possible to control driving of the arm unit 420, for example, expanding or contracting (folding) the arm unit 420. Here, driving of the active joint portions 421a to 421f may be controlled by known body cooperative control and ideal joint control. Since the active joint portions 421a to 421f have the rotation mechanism as described above, in the following description, driving control of the active joint portions 421a to 421f specifically refers to control of a rotational angle and/or a generated torque (torque caused to be generated by the active joint portions 421a to 4210 of the active joint portions 421a to 421f.

The passive sliding mechanism 100 is a mode of a passive form changing mechanism, and connects the link 422c and the link 422d such that the link 422c and the link 422d are able to reciprocate relative to each other in a predetermined direction. For example, the passive sliding mechanism 100 may connect the link 422*c* and the link 422*d* such that the link 422*c* and the link 422*d* are able to linearly move relative to each other. However, the reciprocating movement of the link 422*c* and the link 422*d* is not limited to the linear movement and may also be a reciprocating movement in a direction forming an arc shape. For example, a reciprocating operation of the passive sliding mechanism 100 is performed by a user, and a distance between the active joint portion 421*c* at one end side of the link 422*c* and the passive joint portion 200 is set to vary. Consequently, an overall form of the arm unit 420 can be changed. Details of the configuration of the passive sliding mechanism 100 will be described below.

The passive joint portion 200 is a mode of a passive form changing mechanism, and connects the link 422*d* and the link 422*e* such that the link 422*d* and the link 422*e* are able to rotate relative to each other. For example, a rotating operation of the passive joint portion 200 is performed by the user, and an angle formed between the link 422*d* and the link 422*e* is set to vary. Consequently, an overall form of the arm unit 420 can be changed. Details of the configuration of the passive joint portion 200 will be described below.

In the present specification, "attitude of an arm unit" refers to a state of an arm unit that can be changed by driving control of the actuator provided at the active joint portions 421*a* to 421*f* by a control unit in a state in which a distance between neighboring active joint portions with one or a plurality of links sandwiched therebetween is constant. Also, "form of an arm unit" refers to a state of an arm unit that can be changed due to a change in a distance between neighboring active joint portions with links sandwiched therebetween or a change in an angle formed between the links connecting the neighboring active joint portions in accordance with the passive form changing mechanism being operated.

The supporting arm apparatus 400 according to the present embodiment has six active joint portions 421*a* to 421*f*, and six degrees of freedom is realized therein with respect to driving of the arm unit 420. That is, while driving control of the supporting arm apparatus 400 is realized by driving control of the six active joint portions 421*a* to 421*f* by the control unit, the passive sliding mechanism 100 and the passive joint portion 200 are not subject to driving control by the control unit.

Specifically, as illustrated in FIG. 18, the active joint portions 421*a*, 421*d*, and 421*f* are provided such that long-axis directions of the links 422*a* and 422*e* connected to the active joint portions 421*a* and 421*d*, respectively, and an imaging direction of the endoscope apparatus 423 connected to the 421*f* are set to be rotation axis directions of the active joint portions 421*a*, 421*d*, and 421*f*. The active joint portions 421*b*, 421*c*, and 421*e* are provided such that an x-axis direction, which is a direction in which connection angles of each of the links 422*a* to 422*c*, 422*e*, 422*f*, and the endoscope apparatus 423 connected to the active joint portions 421*b*, 421*c*, and 421*e* are changed in a y-z plane (the plane defined by the y-axis and the z-axis), is set to be a rotation axis direction. As described above, in the present embodiment, the active joint portions 421*a*, 421*d*, and 421*f* have a function of performing so-called yawing, and the active joint portions 421*b*, 421*c*, and 421*e* have a function of performing so-called pitching.

By having such a configuration of the arm unit 420, since six degrees of freedom is realized with respect to driving of the arm unit 420 in the supporting arm apparatus 400 according to the present embodiment, it is possible to cause the endoscope apparatus 423 to freely move within a movable range of the arm unit 420. In FIG. 18, a hemisphere is illustrated as an example of a movable range of the endoscope apparatus 423. If a central point RCM (remote center of movement) of the hemisphere is an imaging center of a treatment site imaged by the endoscope apparatus 423, by causing the endoscope apparatus 423 on a spherical surface of the hemisphere in a state in which the imaging center of the endoscope apparatus 423 is fixed to the central point of the hemisphere, it is possible to image the treatment site from various angles.

The configuration of the supporting arm apparatus 400 according to the present embodiment has been described above. Hereinafter, a configuration example of a controlling apparatus for performing driving control of the arm unit 420, that is, control of rotation driving of an actuator 430 provided at the active joint portions 421*a* to 421*f*, in the supporting arm apparatus 400 according to the present embodiment will be described.

Figure 19:
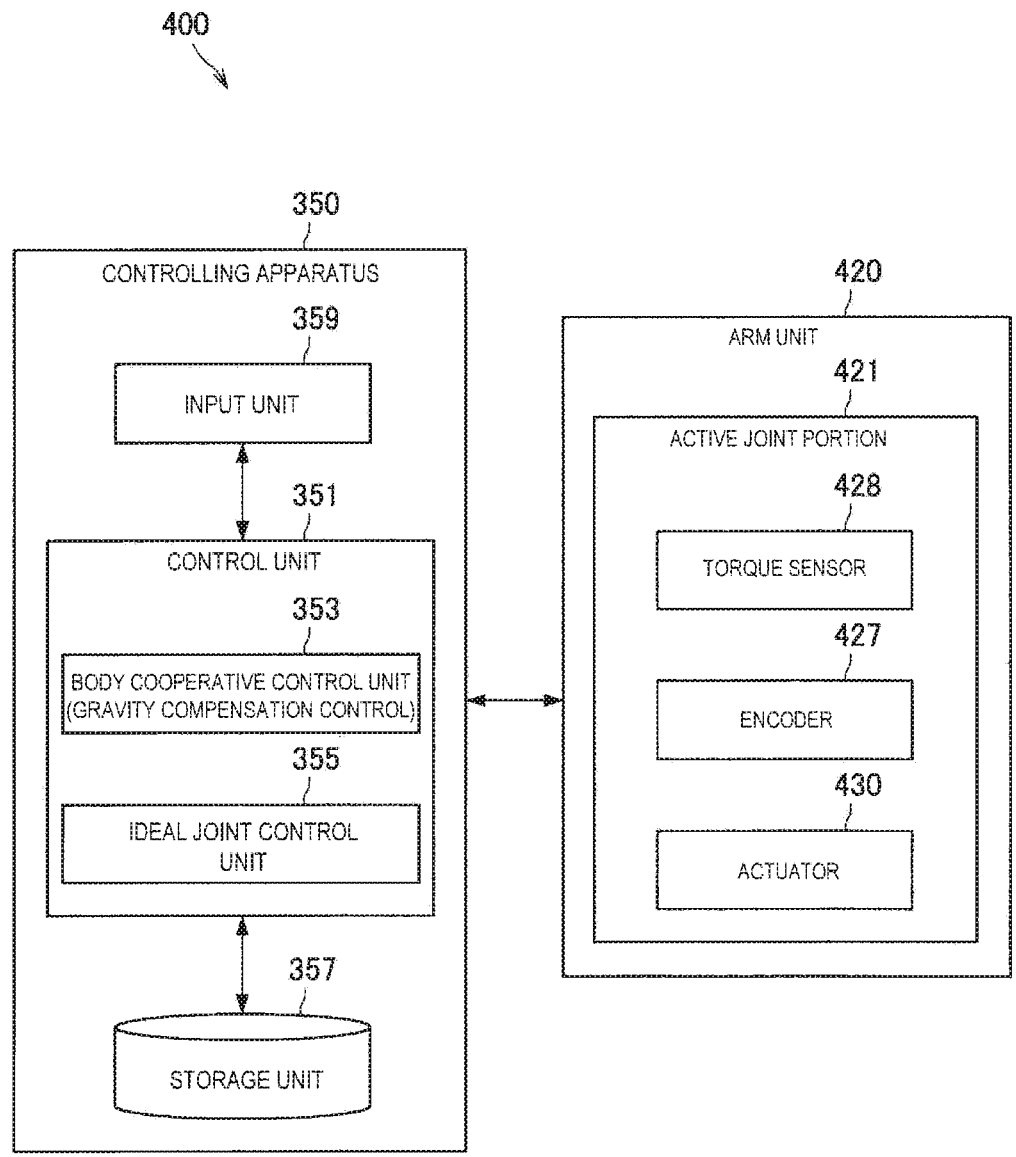
FIG. 19 is a block diagram illustrating the configuration example of the medical supporting arm apparatus.

FIG. 19 is a block diagram illustrating an overall configuration example of the supporting arm apparatus 400 including a controlling apparatus 350. The controlling apparatus 350 includes a control unit 351, a storage unit 357, and an input unit 359.

The control unit 351 includes of various signal processing circuits such as a CPU and a DSP. The control unit 351 integrally controls the controlling apparatus 350 and performs various arithmetic operations for controlling driving of the arm unit 420 in the supporting arm apparatus 400. Specifically, the control unit 351 has a body cooperative control unit 353 and an ideal joint control unit 355. The body cooperative control unit 353 performs various arithmetic operations in the body cooperative control to drive-control the actuator 430 provided at the active joint portions 421*a* to 421*f* of the arm unit 420 of the supporting arm apparatus 400. The ideal joint control unit 355 various arithmetic operations in the ideal joint control that realizes an ideal response to the body cooperative control by correcting an influence of disturbance. The storage unit 357 may be a storage element such as a random access memory (RAM) or a read-only memory (ROM) or may be a semiconductor memory, a hard disk, or an external storage device.

The input unit 359 is an inputting interface through which the user inputs information, instructions, or the like related to the driving control of the supporting arm apparatus 400 to the control unit 351. The input unit 359 may have an operation section operated by the user such as a lever and a pedal, and in accordance with operation of the lever, the pedal, or the like, the position, speed, or the like of each component of the arm unit 420 may be set for a purpose of instantaneous movement. Such an input unit 359 may have an operation section operated by the user such as a mouse, a keyboard, a touch panel, a button, and a switch, in addition to the lever or pedal.

The arm unit 420 controlled by the controlling apparatus 350 includes active joint portions 421. The active joint portions 421 (421*a* to 421o have various configurations necessary for driving of the arm unit 420, such as support members for connecting or supporting the links 422*a* to 422*f* and the endoscope apparatus 423. In the above description and the following description, driving of a joint portion of the arm unit 420 may refer to driving of the actuator 430 in the active joint portions 421*a* to 421*f*.

The active joint portion 421 includes a torque sensor 428, an encoder 427, and the actuator 430. Although the actuator 430, the encoder 427, and the torque sensor 428 are separately illustrated in FIG. 19, the encoder 427 and the torque sensor 428 may be included in the actuator 430

The actuator 430 includes a motor, a motor driver, and a decelerator. The actuator 430 is, for example, an actuator corresponding to force control. In the actuator 430, rotation of the motor is decelerated at a predetermined deceleration ratio by the decelerator and transmitted to another member at a rear stage through an output shaft so that the other member is driven.

The motor is a driving mechanism that causes a rotation driving force to be generated. By control from the motor driver, the motor is driven to generate torque corresponding to a torque command value from the control unit. For example, a brushless motor is used as the motor. However, the present embodiment is not limited to such an example, and various other known types of motor may be used as the motor.

The motor driver is a driver circuit (driver integrated circuit (IC)) that causes the motor to be rotation-driven by supplying a current to the motor, and can control a number of rotations of the motor by adjusting an amount of current supplied to the motor. The motor driver causes the motor to be driven by supplying a current corresponding to a torque command value T from the control unit to the motor.

The motor driver may adjust a viscosity resistance coefficient in rotation of the actuator 430 by adjusting the amount of current supplied to the motor. Consequently, it becomes possible to apply a predetermined resistance to rotation of the actuator 430, that is, rotation of the active joint portions 421a to 421f. For example, the active joint portions 421a to 421f may be set to a state in which it is easy for the active joint portions 421a to 421f to rotate against a force applied from the outside (that is, a state in which it is easy to move the arm unit 420 manually), or conversely, set to a state in which it is difficult for the active joint portions 421a to 421f to rotate against a force applied from the outside (that is, a state in which it is difficult to move the arm unit 420 manually). The above-described all-free mode is realized by making the active joint portions 421a to 421f to be in a state in which it is easy for the active joint portions 421a to 421f to rotate against a force applied from the outside.

The decelerator is connected to a rotation shaft (driving shaft). The decelerator decelerates a rotational speed of the rotation shaft (that is, a rotational speed of an input shaft) of the motor connected thereto at a predetermined deceleration ratio and transmits the decelerated rotational speed to the output shaft. In the present embodiment, a configuration of the decelerator is not limited to a specific type, and various known types of decelerators may be used as the decelerator. However, preferably, a decelerator capable of setting a deceleration ratio with high precision, such as a harmonic drive (registered trademark), is used as the decelerator. The deceleration ratio of the decelerator may be suitably set in accordance with a purpose of the actuator 430. For example, in a case in which the actuator 430 is applied to the active joint portions 421a to 421f of the supporting arm apparatus 400 as in the present embodiment, a decelerator having a deceleration ratio of about 1:100 may be suitably used.

The encoder 427 detects a rotational angle of the input shaft (that is, a rotational angle of the rotation axis of the motor). On the basis of the number of rotations of the input shaft detected by the encoder 427 and the deceleration ratio of the decelerator, pieces of information such as rotational angles, rotational angular speeds, and rotational angular accelerations of the active joint portions 421a to 421f may be obtained. Various known rotary encoders such as a magnetic type encoder and an optical type encoder may be used as the encoder 427. The encoder 427 may be provided only at the input shaft of the actuator 430, and an encoder for detecting a rotational angle or the like of the output shaft of the actuator 430 may be further provided behind the decelerator.

The torque sensor 428 is connected to the output shaft of the actuator 430 and detects torque that acts on the actuator 430. The torque sensor 428 detects torque (generated torque) that is output by the actuator 430. The torque sensor 428 may also detect external torque that is applied from the outside to the actuator 430.

The configuration of the active joint portion 421 has been described above. Here, in the present embodiment, operation of the arm unit 420 is controlled by force control. In the force control, in the supporting arm apparatus 400, a rotational angle of each of the active joint portions 421a to 421f and a torque that acts on each of the active joint portions 421a to 421f are detected by the encoder 427 and the torque sensor 428 provided in each actuator 430. At this time, the torque that acts on each of the active joint portions 421a to 421f detected by the torque sensor 428 may include a force that acts on the arm unit 420 and/or the endoscope apparatus 423.

A current state (position, speed, and the like) of the arm unit 420 can be acquired on the basis of the rotational angle detected by the encoder 427 and the torque value detected by the torque sensor 428. In the supporting arm apparatus 400, a torque that the actuator 430 provided in each of the active joint portions 421a to 421f has to generate which is necessary for the arm unit 420 to execute a desired movement purpose is calculated on the basis of the acquired state of the arm unit 420 (arm state), and the actuator 430 of each of the active joint portions 421a to 421f is caused to be driven by using the torque as a control value.

Various known actuators which are generally used in various apparatuses whose operations are controlled by force control can be used as the actuator 430. For example, as the actuator 430, those disclosed in JP 2009-269102A and JP 2011-209099A, which are patent applications previously filed by the present applicant, can be suitably used.

In the supporting arm apparatus 400 according to the present embodiment, configurations of the actuator 430 and each component of the actuator are not limited to the above-described configurations, and the actuator 430 and each component thereof may have different configurations.

11. Configuration Example in which Only Actuator at Endoscope Side is Provided In the above description, the medical holding apparatus 100 including the two actuators 110 and 120 has been described. On the other hand, the medical holding apparatus 100 may include only a single actuator. In this case, rotation of the endoscope 300 relative to the camera head 200 is realized by having a rotation mechanism for causing the endoscope 300 to rotate relative to the camera head 200 and at least one actuator mounted.

Figure 20:
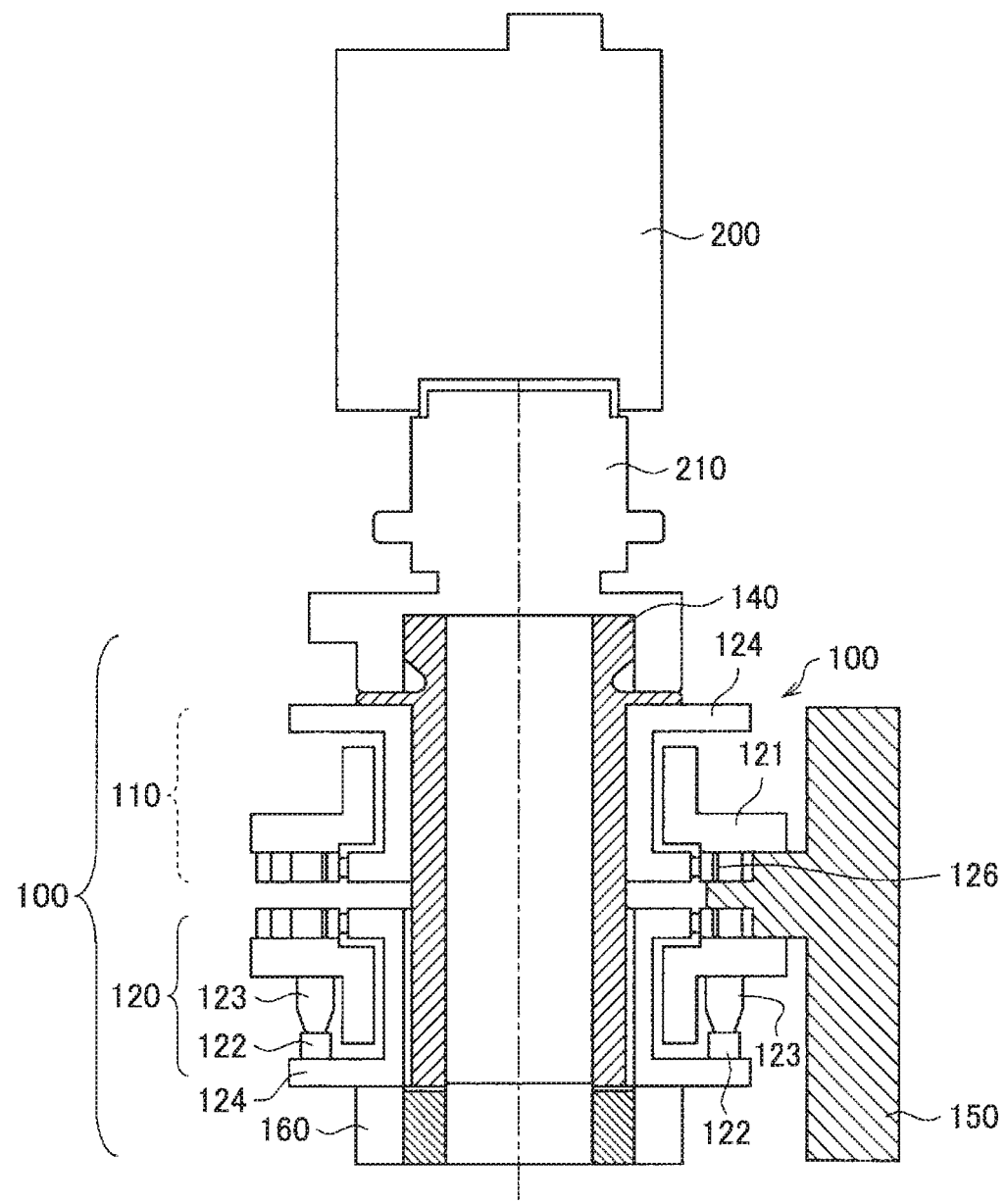
FIG. 20 is a schematic diagram illustrating a medical holding apparatus in a case in which the medical holding apparatus includes a single actuator.

FIG. 20 is a schematic diagram illustrating the medical holding apparatus 100 in a case in which the medical holding apparatus 100 includes a single actuator. In an example illustrated in FIG. 20, only the actuator 120 is provided from among the two actuators 110 and 120 illustrated in FIG. 2. Also, in the example illustrated in FIG. 20, although not all configurations of the actuator 110 illustrated in FIG. 2 are provided, the configurations other than the stator 123 and the rotor 122 are provided from among the configurations of the actuator 110. Specifically, the fixing frame 121, the output unit 124, and the bearing unit 126 are provided from among the configurations of the actuator 110 illustrated in FIG. 2. For this reason, the output unit 124 is supported to be able to freely rotate relative to the fixing frame 121 by the bearing unit 126, and consequently, the rotation mechanism that causes the camera head 200 to freely rotate is realized.

Therefore, according to the configuration of the medical holding apparatus 100 illustrated in FIG. 20, same as the medical holding apparatus 100 illustrated in FIG. 2, by driving the actuator 120 provided at the endoscope 300 side, the adaptor 160 and the drape mounting unit 600 rotate together with the output unit 124, and the endoscope 300 mounted at the drape mounting unit 600 integrally rotates with the drape mounting unit 600. Consequently, the endoscope 300 can rotate relative to the frame 150.

On the other hand, according to the configuration of the medical holding apparatus 100 illustrated in FIG. 20, unlike the medical holding apparatus 100 illustrated in FIG. 2, the stator 123 and the rotor 122 are not provided from among the configurations of the actuator 110 at the camera head 200 side. For this reason, the output unit 124 can rotate freely relative to the fixing frame 121 by the bearing unit 126, and the lens barrel 140 fixed to the output unit 124 can also rotate freely relative to the fixing frame 121. Therefore, the lens barrel 140, the endoscope adaptor 210, and the camera head 200 can be rotated freely relative to the frame 150. Consequently, since the camera head 200 can be rotated freely relative to the frame 150, for example, by the surgeon causing the camera head 200 to rotate by hand, a top-and-bottom direction of an image that is imaged by the camera head 200 can be caused to change freely.

Regarding control of the top-and-bottom direction of the camera head 200, a weight is attached at a position shifted from a rotation axis (an optical axis of the camera head 200) of members such as the output unit 124 and the endoscope adaptor 210 that hold the camera head 200, and the top-and-bottom direction of the camera head 200 can be controlled by self-weight of the weight. Note that it is not necessary for a weight attachment position to be a position shifted from the rotation axis. For example, a weight whose center of mass is shifted from the rotation axis may be attached on the rotation axis so as to control the top-and-bottom direction. That is, the weight may rotate in the direction of gravity due to the center of mass of the weight being shifted from the rotation axis, and the top-and-bottom direction of the camera head 200 can be controlled.

Figure 21:
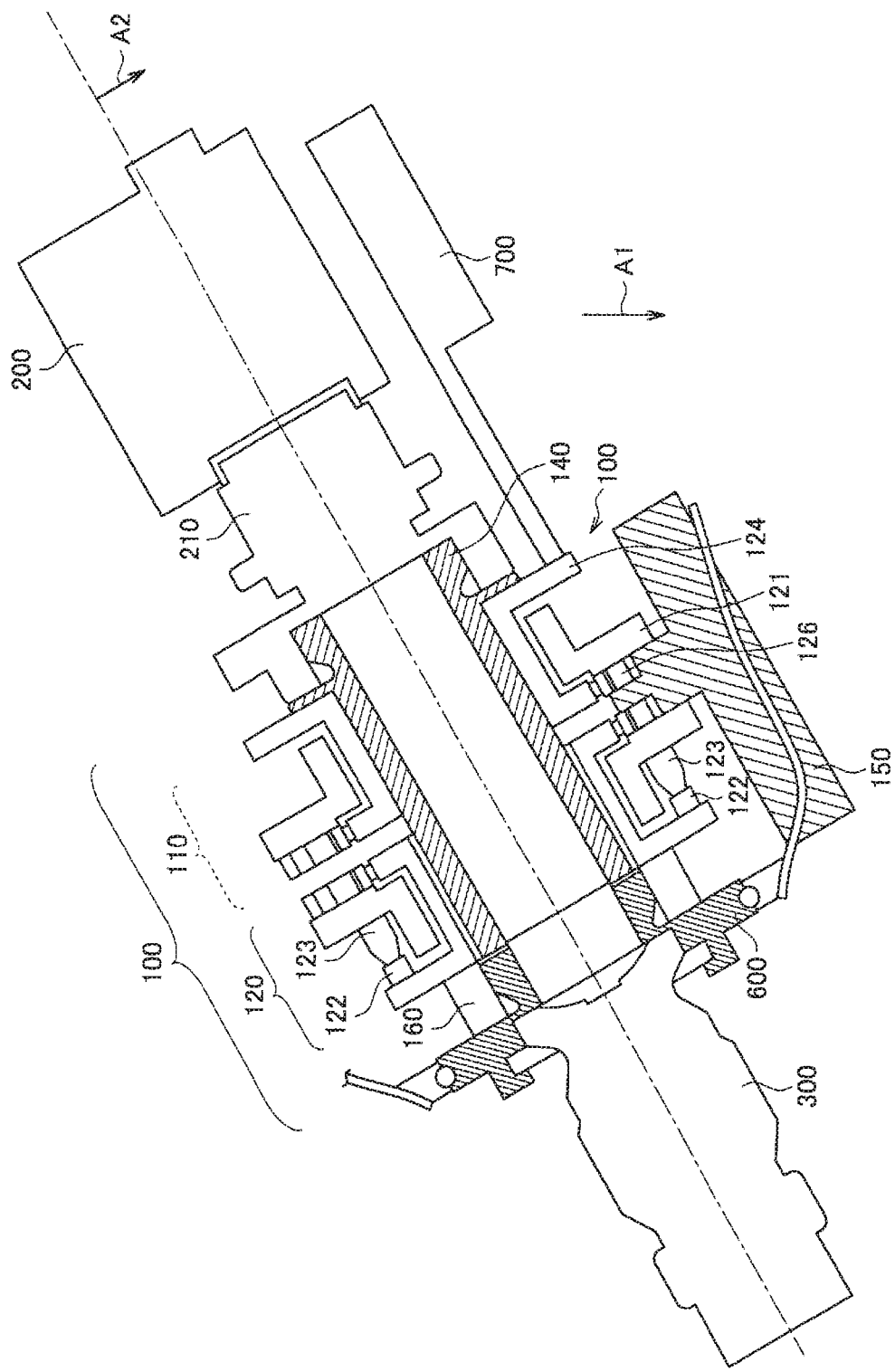
FIG. 21 is a schematic diagram illustrating a state in which a rotation axis of the medical holding apparatus 100 illustrated in FIG. 20 is disposed to be inclined with respect to the direction of gravity.

FIG. 21 is a schematic diagram illustrating a state in which a rotation axis of the medical holding apparatus 100 illustrated in FIG. 20 is disposed to be inclined with respect to the direction of gravity. As illustrated in FIG. 21, a weight 700 is attached to the output unit 124 corresponding to the actuator 110 illustrated in FIG. 2. In FIG. 21, a direction indicated by an arrow A1 is the direction of gravity, and a direction indicated by an arrow A2 is the top-and-bottom direction of the camera head 200. By the output unit 124 rotating due to the self-weight of the weight 700 and the weight 700 descending in the direction of gravity, the output unit 124, the endoscope adaptor 210, and the camera head 200 rotate integrally and the weight 700 is disposed at the lowermost point. In this way, the top-and-bottom direction of the camera head 200 corresponds to the direction of gravity. Consequently, the actuator 110 configured to cause the camera head 200 to rotate relative to the frame 150 may not be provided, and the top-and-bottom direction of the camera head 200 may be controlled to be the direction of gravity. By making the position of the weight 700 relative to the rotation axis to be shifted from the top-and-bottom direction of the camera head 200, an angle of the camera head 200 when the weight 700 is disposed at the lowermost point can be arbitrarily set.

In the medical holding apparatus 100 illustrated in FIG. 20, configurations other than the stator 123 and the rotor 122 are provided from among the configurations of the actuator 110 illustrated in FIG. 2. For this reason, the ring-shaped magnet 128 and the sensor 130, which constitute the magnetic type encoder, illustrated in FIG. 3 are provided. Therefore, a signal corresponding to a position of the magnet 128 is detected by the sensor 130 in response to rotation of the magnet 128, and consequently, a rotational position of the output unit 124 is detected.

For this reason, a rotational position of the camera head 200 can be acquired on the basis of the rotational position of the output unit 124 detected by the magnetic type encoder, and the top-and-bottom direction of the camera head 200 can be acquired. When the top-and-bottom direction of the camera head 200 is known, an image picked up by the camera head 200 is subject to image processing so that the top-and-bottom direction of the picked-up image is displayed correctly. In this case, the image processing unit 5061 illustrated in FIG. 17 performs image processing of the image picked up by the camera head 200 on the basis of the rotational position of the output unit 124 detected by the magnetic type encoder. For example, in a case in which the top-and-bottom direction of the camera head 200 corresponds to the rotational position (=0) of the output unit 124, when the rotational position of the output unit 124 detected by the magnetic type encoder is 30°, the picked-up image is caused to rotate 30° by image processing. Consequently, it is possible to correct so that the top-and-bottom direction of the picked-up image is correct, and it is possible to optimize the top-and-bottom direction of the picked-up image.

As described above, according to the medical holding apparatus 100 illustrated in FIG. 20, by having the single actuator 120 mounted, it is possible to rotate the endoscope 300 relative to the frame 150 by driving of the actuator 120. At the camera head 200 side, it is possible to rotate the camera head 200 freely relative to the frame 150. Consequently, the medical holding apparatus 100 can have a simpler configuration, and the manufacturing cost can be reduced.

Regarding the control of the top-and-bottom direction of the camera head 200, the top-and-bottom direction can be optimally controlled by attaching the weight 700 or by detecting the rotational position of the camera head 200 and performing image processing.

As described above, according to the present embodiment, it is possible to rotate the camera head 200 and the endoscope 300 independently. Consequently, for example, it becomes possible to realize rotation of the endoscope 300 in a state in which the top and bottom of the camera head 200 are held. Also, it becomes possible to secure the clean area using the drape mounting unit 600, and it is possible to realize adaptation of a medical arm, which has a medical holding mechanism mounted, in endoscopic surgical operation using an oblique viewing endoscope.

By providing the drape mounting unit 600 with the rotation mechanism, since it is possible to suppress entanglement of the drape when the endoscope 300 is caused to rotate 360°, it becomes possible to realize free rotation of the endoscope 300 by 360° or more.

By introducing the medical holding apparatus 100, which corresponds to rotation of the endoscope 300, to the medical site, since it is possible to improve on-site occupancy rate, personnel reduction becomes possible by substituting for people. Furthermore, it can be assumed that a machine realizes an oblique viewing endoscope rotating task, which is considered to be difficult to operate, on behalf of people. In addition, it is possible to improve economic feasibility of an endoscope holder by corresponding to general-purpose medical cameras and endoscopes.

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical holding apparatus including:

a first actuator configured to cause a medical optical tool that guides light from a body cavity of a subject to a camera head during a surgical operation, to rotate about an optical axis of the medical optical tool; and a rotation mechanism configured to support the camera head that acquires an image of the body cavity of the subject via the medical optical tool, the camera head being rotatable about the optical axis of the medical optical tool independently from the medical optical tool.

(2)

The medical holding apparatus according to (1), including:

a second actuator configured to cause the camera head to rotate about the optical axis of the medical optical tool.

(3)

The medical holding apparatus according to (1), including:

a weight having a center of mass at a position shifted from the optical axis of the camera head, wherein, due to the weight, the camera head rotates about the optical axis of the medical optical tool through the rotation mechanism.

(4)

The medical holding apparatus according to (1)-(3), wherein the rotation mechanism includes an encoder configured to detect a rotational position of the camera head, and a vertical orientation of the acquired image of the body cavity of the subject that is acquired by the camera head is optimized by image processing in accordance with the rotational position detected by the encoder.

(5)

The medical holding apparatus according to (1)-(4), wherein the medical optical tool is a rigid endoscope.

(6)

The medical holding apparatus according to (1)-(5), wherein the rigid endoscope is an oblique viewing endoscope.

(7)

The medical holding apparatus according to (1)-(6), wherein the first actuator includes a stator fixed to a frame, and a rotor that is rotated by the stator and integrally rotates with the medical optical tool.

(8)

The medical holding apparatus according to (2)-(7), wherein the second actuator includes a stator fixed to a frame, and a rotor that is rotated by the stator and integrally rotates with the camera head.

(9)

The medical holding apparatus according to (2)-(8), wherein the first actuator and the second actuator have hollow shapes, and the optical axis of the medical optical tool and the optical axis of the camera head pass through the hollow shapes.

(10)

The medical holding apparatus according to claim (1)-(9), including:

a lens barrel inside the hollow shapes.

(11)

The medical holding apparatus according to 10, wherein the lens barrel and the camera head integrally rotate by driving of the second actuator.

(12)

The medical holding apparatus according to (1)-(11), including a drape mount configured to separate a clean area and an unclean area, wherein the medical optical tool is connected to an interface device, which is configured to apply a driving force of the first actuator, through the drape mount, and rotates together with the interface device and the drape mount.

(13)

The medical holding apparatus according to (12), wherein the drape mount has a circular outer shape having the optical axis of the medical optical tool as a central axis, and the outer shape of the drape mount is fitted to a fixing member, and the drape mount rotates relative to the fixing member.

(14)

The medical holding apparatus according to (12)-(13), wherein an O-ring is inserted between the outer shape of the drape mount and the fixing member.

(15)

The medical holding apparatus according to (12)-(14), wherein the clean area and the unclean area are separated from each other by the drape mount, the fixing member, and the O-ring.

(16)

The medical holding apparatus according to (2)-(11) including:

a detachable mount that attaches or detaches the camera head to or from an interface device configured to apply a driving force of the second actuator.

(17)

The medical holding apparatus according to (2)-(11) including a frame configured to support the first actuator and the second actuator and to be mounted at a distal end of a medical supporting arm apparatus.

(18)

The medical holding apparatus according to (2)-(11), wherein the first actuator and the second actuator include a ring-shaped ultrasonic motor.

(19)

The medical holding apparatus according to (2)-(11), wherein the first actuator and the second actuator are driven in a no-load state.

(20)

The medical holding apparatus according to (2)-(11), wherein the first actuator rotates in conjunction with the second actuator.

(21)

The medical holding apparatus according to (2)-(11), wherein driving of the first actuator is stopped and the second actuator controls a vertical orientation of capture by the camera head.

(22)

The medical holding apparatus according to (2)-(11), wherein driving of a first one of the first actuator and the second actuator is stopped, and a second one of the first actuator and the second actuator is driven in a no-load state.

(23)

A medical arm system including:
a medical holding apparatus including
a first actuator configured to cause a medical optical tool that guides light from a body cavity of a subject during a surgical operation to rotate about an optical axis of the medical optical tool, and
a second actuator configured to cause a camera head that further acquires the image of the body cavity of the subject via the medical optical tool, the camera head being rotatable about the optical axis of the medical optical tool independently from the medical optical tool; and
a supporting arm having a distal end to which the medical holding apparatus is fixed.

(24)

A drape mounting mechanism including:
a drape mount connected to a medical optical tool for that guides light from a body cavity of a subject during a surgical operation and configured to rotate together with the medical optical tool about an optical axis of the medical optical tool.

(25)

The drape mounting mechanism according to (24), wherein
the drape mount has a circular outer shape having the optical axis of the medical optical tool as a central axis, and
the outer shape of the drape mount is fitted to a fixing member, and the drape mount rotates relative to the fixing member.

(26)

The drape mounting mechanism according to (24)-(26), wherein an O-ring is inserted between the outer shape of the drape mount and the fixing member.

(27)

The drape mounting mechanism according to (24)-(27), wherein a clean area and an unclean area are separated from each other by the drape mount, the fixing member, and the O-ring.

REFERENCE SIGNS LIST 100 medical holding apparatus
110, 120 actuator
122 rotor
123 stator
140 lens barrel
150 frame
200 camera head
300 endoscope
500 medical supporting arm apparatus
600 drape mounting unit
640 O-ring
700 weight

The invention claimed is:

1. A medical holding apparatus comprising:
a first actuator configured to cause medical optical tool that guides light from a body cavity of a subject to a camera head during a surgical operation, to rotate about an optical axis of the medical optical tool;
a second actuator configured to cause the camera head to rotate about the optical axis of the medical optical tool, wherein the first actuator and the second actuator have hollow shapes, and the optical axis of the medical optical tool and an optical axis of the camera head pass through the hollow shapes; and
a rotation mechanism configured to support the camera head that acquires an image of the body cavity of the subject via the medical optical tool,
the camera head being rotatable about the optical axis of the medical optical tool independently from the medical optical tool.

2. The medical holding apparatus according to claim 1, comprising
a weight having a center of mass at a position shifted from the optical axis of the camera head,
wherein, due to the weight, the camera head rotates about the optical axis of the medical optical tool through the rotation mechanism.

3. The medical holding apparatus according to claim 1, wherein
the rotation mechanism includes an encoder configured to detect a rotational position of the camera head, and
a vertical orientation of the acquired image of the body cavity of the subject that is acquired by the camera head is optimized by image processing in accordance with the rotational position detected by the encoder.

4. The medical holding apparatus according to claim 1, wherein the medical optical tool is a rigid endoscope.

5. The medical holding apparatus according to claim 4, wherein the rigid endoscope is an oblique viewing endoscope.

6. The medical holding apparatus according to claim 1, wherein the first actuator includes a stator fixed to a frame, and a rotor that is rotated by the stator and integrally rotates with the medical optical tool.

7. The medical holding apparatus according to claim 1, wherein the second actuator includes a stator fixed to a frame, and a rotor that is rotated by the stator to be integrally rotated with the camera head.

8. The medical holding apparatus according to claim 1, comprising
a lens barrel inside the hollow shapes.

9. The medical holding apparatus according to claim 8, wherein the second actuator is configured to integrally rotate the lens barrel and the camera.

10. The medical holding apparatus according to claim 1, comprising
a drape mount configured to separate a clean area and an unclean area,
wherein the medical optical tool is connected to an interface device, which is configured to apply a driving force of the first actuator, through the drape mount, and rotates together with the interface device and the drape mount.

11. The medical holding apparatus according to claim 10, wherein
the drape mount has a circular outer shape having the optical axis of the medical optical tool as a central axis, and
the outer shape of the drape mount is fitted to a fixing member, and the drape mount rotates relative to the fixing member.

12. The medical holding apparatus according to claim 11, wherein an O-ring is inserted between the outer shape of the drape mount and the fixing member.

13. The medical holding apparatus according to claim 12, wherein the clean area and the unclean area are separated from each other by the drape mount, the fixing member, and the O-ring.

14. The medical holding apparatus according to claim 1, comprising
a detachable mount that is configured to attach or detach the camera head to or from an interface device configured to apply a driving force of the second actuator.

15. The medical holding apparatus according to claim 1, comprising
a frame configured to support the first actuator and the second actuator and to be mounted at a distal end of a medical supporting arm apparatus.

16. The medical holding apparatus according to claim 1, wherein the first actuator and the second actuator each include a ring-shaped ultrasonic motor.

17. The medical holding apparatus according to claim 1, further comprising driving circuitry to drive the first actuator and the second actuator in a no-load state.

18. The medical holding apparatus according to claim 1, wherein the first actuator rotates in conjunction with the second actuator.

19. The medical holding apparatus according to claim 1, further comprising driving circuitry to stop driving of the first actuator and drive the second actuator to control a vertical orientation of capture by the camera head.

20. The medical holding apparatus according to claim 1, further comprising driving circuitry to stop driving of a first one of the first actuator and the second actuator, and drive a second one of the first actuator and the second actuator in a no-load state.

* * * * *